(12) United States Patent
Ozawa et al.

(10) Patent No.: US 8,470,974 B2
(45) Date of Patent: Jun. 25, 2013

(54) METHOD FOR HIGHLY SENSITIVE DETECTION OF PROTEIN-PROTEIN INTERACTION

(75) Inventors: Takeaki Ozawa, Tokyo (JP); Naomi Misawa, Tokyo (JP); Kenji Miura, Tokyo (JP); Tasuku Okamoto, Tokyo (JP); Shigeaki Nishii, Tokyo (JP); Kenji Masuda, Tokyo (JP)

(73) Assignees: The University of Tokyo, Tokyo (JP); ProbeX Inc., Tokyo (JP); Tokyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 13/375,142

(22) PCT Filed: May 28, 2010

(86) PCT No.: PCT/JP2010/059160
§ 371 (c)(1),
(2), (4) Date: Apr. 12, 2012

(87) PCT Pub. No.: WO2010/137717
PCT Pub. Date: Dec. 2, 2010

(65) Prior Publication Data
US 2012/0190824 A1    Jul. 26, 2012

(30) Foreign Application Priority Data

May 29, 2009  (JP) ................ 2009-131481
Feb. 23, 2010  (JP) ................ 2010-037921

(51) Int. Cl.
*C07K 1/00*        (2006.01)
*C12Q 1/00*        (2006.01)
*G01N 33/53*       (2006.01)
*C12P 21/04*       (2006.01)
*A61K 39/02*       (2006.01)

(52) U.S. Cl.
USPC ............... 530/350; 435/4; 435/7.1; 435/69.7; 424/190.1

(58) Field of Classification Search
None
See application file for complete search history.

(56) References Cited

U.S. PATENT DOCUMENTS

2008/0233589 A1 * 9/2008 Piwnica-Worms ............ 435/6

FOREIGN PATENT DOCUMENTS

| EP | 1956086 | 8/2008 |
| JP | 2007-159567 | 6/2007 |
| JP | 2008-289475 | 12/2008 |
| JP | 2008-289475 A | 12/2008 |
| WO | WO2007/027919 | 3/2007 |

OTHER PUBLICATIONS

Misawa N. et al. Rapid and High-Sensitivity Cell-Based Assays of Protein-Protein Interactions Using Split Click Beetle luciferase Complmentation: An Approach to the Study of G-Protein-Coupled Receptors. Analytical Chemistry. 82(6):2552-2560. Published on Web Feb. 24, 2010.*
Hida N. et al. High-Sensitivity Real-time Imaging of Dual Protein-Protein Interactions in Living Subjects Using Multicolor Luciferases. PLoS One. 4(6):e5868. Jun. 12, 2009.*
Kim et al. Circularly Permutated Bioluminescent Probes for Illuminating Ligand-Activated Protein Dynamics. Bioconjugate Chemistry. 19(12):2480-2486. Published on Web Dec. 2, 2008.*
Kim et al. Circularly permutated bioluminescent probes for illuminating ligand-activated protein dynamics. Bioconjugate Chemistry. 19(12):2480-2486, published Dec. 2, 2008.*
PCT International Search Report prepared for PCT/JP2010/059160 mailed Aug. 10, 2010.
Kim et al., "High-throughput sensing and noninvasive imaging of protein nuclear transport by using reconstitution of split *Renilla* luciferase," Proc. Natl. Acad. Sci., vol. 101, No. 32, pp. 11542-11547, Aug. 10, 2004.

* cited by examiner

*Primary Examiner* — Vanessa L Ford
*Assistant Examiner* — Sandra Dillahunt
(74) *Attorney, Agent, or Firm* — Barnes & Thornburg LLP

(57) ABSTRACT

The present invention intends to provide an assay system using split luciferase that has a remarkably high detection sensitivity. In an embodiment, binding of mutually binding first and second proteins is detected by preparing a first fusion protein comprising the first protein fused with a peptide having the amino acid sequence of amino acid SEQ ID NO: 1 and a second fusion protein comprising the second protein fused with a peptide having an amino acid sequence selected from the group consisting of amino acid SEQ ID NOS: 2 to 6, and allowing the first fusion protein to bind with the second fusion protein to form a complex, and detecting luminescence emitted from the complex.

13 Claims, 15 Drawing Sheets

```
   1 atggagagagaagaacgtggtgtacggccccgagcccaagcaccctctgggcaacttcaccgcccggcgagtgctgtacaacgctctg
     M  E  R  E  K  N  V  V  Y  G  P  E  P  K  H  P  L  G  N  F  T  A  G  E  M  L  Y  N  A  L
  91 cacaagcactccacatccccagccatcctggacgtgatgggcaacgagtccctttctaccaggagttctttgacactgtgaag
     H  K  H  S  H  I  P  Q  A  I  L  D  V  M  G  N  E  S  L  S  Y  Q  E  F  F  D  T  T  V  K
 181 ctgggccagagcctccagaactgtgtaccagatgaacgatgtcgtctgcatcgtgcagagaacaacaagagattcttcatccccatc
     L  G  Q  S  L  Q  N  C  G  Y  K  M  N  D  V  V  S  I  C  A  E  N  N  K  R  F  F  I  P  I
 271 atctccgcctggtacatcggcatggtggtggcccctgtgaacgaggactatatcccagacgagctgtgtaaagtgaccggcatctccaag
     I  S  A  W  Y  I  G  M  V  V  A  P  V  N  E  D  Y  I  P  D  E  L  C  K  V  T  G  I  S  K
 361 ccgatcctggtcttcaccactaggaagatcctgcctaaggttttggaggttaaagacagaaccaactacataagaggatcatcatactg
     P  I  L  V  F  T  T  R  K  I  L  P  K  V  L  E  V  K  D  R  T  N  Y  I  K  R  I  I  I  L
 451 gactctgaagagaacctgctgggctgcgagagcctgcacaacttcatgtccaggtactccgacaacaactccaaacttcaagcctctg
     D  S  E  E  N  L  L  G  C  E  S  L  H  N  F  M  S  R  Y  S  D  N  N  L  Q  T  F  K  P  L
 541 cactacgaccctgtgacccaggtagccgccatcctgtctcctccggcacaaccggctgcctaaaggcgtgatgcagaccacaggaac
     H  Y  D  P  V  D  Q  V  A  A  I  L  C  S  S  G  T  T  G  L  P  K  G  V  M  Q  T  H  R  N
 631 atctgtgtgagactcacacacagctcatcccccgtatccgtgctggcctacctgccattcttc
     I  C  V  R  L  T  H  A  S  D  P  R  V  G  T  Q  L  I  P  G  V  S  V  L  A  Y  L  P  F  F
 721 cacggccttcaggcttcagtatcaacctgggctatttcatggtgttcatgtcatgcctgagagtggtgatgtccaaggttttaacaggagagttcctg
     H  A  F  G  F  S  I  N  L  G  Y  F  M  V  G  L  R  V  V  M  L  R  R  F  N  Q  E  V  F  L
 811 aaggccatccaggactaccaggagtgagagcgtgatcaacgttccctccacaatcctgtttctgtccaagagccctgtgacaagtac
     K  A  I  Q  D  Y  E  V  R  S  V  I  N  V  P  S  T  I  L  F  L  S  K  S  P  L  V  D  K  Y
 901 gacctatccaccctggccgagctgtgtgctaacagagtctactccgccaacatccatctgcacaacgagttcaagtccggtctccctgggcaag
     D  L  S  T  L  A  E  L  C  C  G  A  A  P  L  A  K  E  V  A  E  I  A  V  K  R  L  N  L  P
 991 gggatacgtgtgtggctacggctacggcctaacagagtctaccgcaacatcactactgcacaaccggcgcatctgtgcatctgggga
     G  I  R  C  G  Y  G  L  T  E  S  T  S  A  N  I  H  T  L  H  N  E  F  K  S  G  S  L  G  K
1081 gtgacacttacatggccgccagatcatcgacagaacaccggcgaggcctggtccaaccaggcctactaaggaggccatcgacgacgacggcatgctccactctggcgacttcggc
     V  T  P  Y  M  A  A  K  I  I  D  R  N  T  G  E  A  L  G  P  N  Q  V  G  E  L  C  I  W  G
1171 cctatgtgtaacaaaaggctatgtgaaccacaaccacccaggctactaaggaggccatcgacgacgacggcatgctccactctggcgacttcggc
     P  M  V  T  K  G  Y  V  N  N  P  Q  A  T  K  E  A  I  D  D  D  G  M  L  H  S  G  D  F  G
1261 tactacgacgaggacgagtattttctatatcgtggacgataggtataaagacctaatcaaggctatgtccccctgtgggagctg
     Y  Y  D  E  D  E  Y  F  F  Y  I  V  D  R  Y  R  K  E  L  I  K  Y  K  G  Y  Q  V  A  P  V  E  L
```

Fig 1-1
(A) (continued)

```
1351 gaggagatcctccttcagcacccaggcatcagggacgtggccgtcgtgggtatccctgacatcgaggccggcgagctgccagcccggcttc
     E  E  I  L  Q  H  P  G  I  R  D  V  A  V  V  G  I  P  D  I  E  A  G  E  L  P  A  G  F
1441 gtggtgaagcagcccggggcccaactcaccgctaaggaggtgtacgacttcctggccgagcggtgtctcactccaagtacctgaggggc
     V  V  K  Q  P  G  A  Q  L  T  A  K  E  V  Y  D  F  L  A  Q  R  V  S  H  S  K  Y  L  R  G
1531 ggcgtaaggttcgtggactctatcccccaggaaacgtgacaggcaagattagtcgaaaagagctgaggaggccctgatggagaaggcttct
     G  V  R  F  V  D  S  I  P  R  N  V  T  G  K  I  S  R  K  E  L  R  E  A  L  M  E  K  A  S
1621 aagctgtaa 1629    (SEQ ID No 70)
     K  L  *         (SEQ ID No 71)
```

Fig 1-2 (B)

| SEQ ID No | primer name | primer sequence |
|---|---|---|
| 13 | N-PtGR-F001 | tttaagcttaccgccatggagagagagaagaac |
| 14 | N-PtGR-R404 | ttttggatcctccgcctcctccagtagcctgtgggttgtt |
| 15 | N-PtGR-R405 | ttttggatcctccgcctcctcccttagtagcctgtgggtt |
| 16 | N-PtGR-R406 | ttttggatcctccgcctcctccctccttagtagcctgtgg |
| 17 | N-PtGR-R407 | ttttggatcctccgcctcctccggcctccttagtagcctg |
| 18 | N-PtGR-R408 | ttttggatcctccgcctcctccgatggcctccttagtagc |
| 19 | N-PtGR-R409 | ttttggatcctccgcctcctccgtcgatggcctccttagt |
| 20 | N-PtGR-R410 | ttttggatcctccgcctcctccgtcgtcgatggcctcctt |
| 21 | N-PtGR-R411 | ttttggatcctccgcctcctccgtcgtcgtcgatggcctc |
| 22 | N-PtGR-R412 | ttttggatcctccgcctcctccgccgtcgtcgtcgatggc |
| 23 | N-PtGR-R413 | ttttggatcctccgcctcctccccagccgtcgtcgtcgat |
| 24 | C-PtGR-F394 | aggctcgagtggaggcggcggaacaaaaggctatgtgaac |
| 25 | C-PtGR-R542 | ttttccgcgggcccagcttagaagccttctc |
| 26 | N-PtGR-R414 | ttttggatcctccgcctcctcccagccagccgtcgtcgtc |
| 27 | N-PtGR-R415 | ttttggatcctccgcctcctccgtgcagccagccgtcgtc |
| 28 | N-PtGR-R416 | ttttggatcctccgcctcctccagagtgcagccagccgtc |
| 29 | N-PtGR-R417 | ttttggatcctccgcctcctccgccagagtgcagccagcc |
| 30 | C-PtGR-F395 | aggctcgagtggaggcggcggaaaaggctatgtgaacaac |
| 31 | C-PtGR-F396 | aggctcgagtggaggcggcggaggctatgtgaacaaccca |
| 32 | C-PtGR-F397 | aggctcgagtggaggcggcggatatgtgaacaacccacag |
| 33 | C-PtGR-F398 | aggctcgagtggaggcggcggagtgaacaacccacaggct |
| 34 | C-PtGR-F399 | aggctcgagtggaggcggcggaaacaacccacaggctact |
| 35 | C-PtGR-F401 | aggctcgagtggaggcggcggaccacaggctactaaggag |
| 36 | C-PtGR-F402 | aggctcgagtggaggcggcggacaggctactaaggaggcc |
| 37 | C-PtGR-F404 | aggctcgagtggaggcggcggaactaaggaggccatcgac |
| 38 | C-PtGR-F405 | aggctcgagtggaggcggcggaaaggaggccatcgacgac |
| 39 | C-PtGR-F406 | aggctcgagtggaggcggcggagaggccatcgacgacgac |
| 40 | C-PtGR-F407 | aggctcgagtggaggcggcggagccatcgacgacgacggc |
| 41 | C-PtGR-F408 | aggctcgagtggaggcggcggaatcgacgacgacggctgg |
| 42 | C-PtGR-F409 | aggctcgagtggaggcggcggagacgacgacggctggctg |
| 43 | C-PtGR-F410 | aggctcgagtggaggcggcggagacgacggctggctgcac |
| 44 | C-PtGR-F411 | aggctcgagtggaggcggcggagacggctggctgcactct |
| 45 | C-PtGR-F412 | aggctcgagtggaggcggcggaggctggctgcactctggc |
| 46 | C-PtGR-F413 | aggctcgagtggaggcggcggatggctgcactctggcgac |
| 47 | C-PtGR-F400-2 | aggctcgagtggaggcggcggaaacccacaggctactaaggag |
| 48 | C-PtGR-F403-2 | aggctcgagtggaggcggcggagctactaaggaggccatcgac |
| 49 | C-PtGR-F393 | aggctcgagtggaggcggcggagtaacaaaaggctatgtg |
| 50 | C-PtGR-F392 | aggctcgagtggaggcggcggaatggtaacaaaaggctat |
| 51 | C-PtGR-F391 | aggctcgagtggaggcggcggacctatggtaacaaaaggc |
| 52 | C-PtGR-F390 | aggctcgagtggaggcggcggaggacctatggtaacaaaa |
| 53 | C-PtGR-F389 | aggctcgagtggaggcggcggatggggacctatggtaaca |

Fig 1-3

(C) (SEQ ID No 7)

aagctt accgcc                                                          [HindIII+Kozac]

```
ATGGAGAGAG AGAAGAACGT GGTGTACGGC CCCGAGCCCA AGCACCCTCT
GGGCAACTTC ACCGCCGGCG AGATGCTGTA CAACGCTCTG CACAAGCACT
CCCACATCCC CCAGGCCATC CTGGACGTGA TGGGCAACGA GTCCCTTTCC
TACCAGGAGT TCTTCGACAC TACTGTGAAG CTGGGCCAGA GCCTCCAGAA
CTGTGGCTAC AAGATGAACG ATGTCGTGTC GATCTGTGCA GAGAACAACA
AGAGATTCTT CATCCCCATC ATCTCCGCCT GGTACATCGG CATGGTGGTG
GCCCCTGTGA ACGAGGACTA TATCCCAGAC GAGCTGTGTA AAGTGACCGG
CATCTCCAAG CCGATCCTGG TCTTCACCAC TAGGAAGATC CTGCCTAAGG
TTTTGGAGGT TAAAGACAGA ACCAACTACA TAAAGAGGAT CATCATACTG
GACTCTGAAG AGAACCTGCT GGGCTGCGAG AGCCTGCACA ACTTCATGTC
CAGGTACTCC GACAACAACC TCCAAACATT CAAGCCTCTG CACTACGACC
CTGTGGACCA GGTAGCCGCC ATCCTGTGCT CCTCCGGCAC AACCGGCCTG
CCTAAAGGCG TGATGCAGAC CCACAGGAAC ATCTGTGTGA GACTCACACA
CGCATCTGAC CCCAGAGTGG GTACACAACT CATCCCCGGC GTATCCGTGC
TGGCCTACCT GCCATTCTTC CACGCCTTCG GCTTCAGTAT CAACCTGGGC
TATTTCATGG TGGGCCTGAG AGTGGTGATG CTCCGAAGGT TTAACCAGGA
GGTGTTCCTG AAGGCCATCC AGGACTACGA GGTGAGGAGC GTGATCAACG
TTCCCTCCAC AATCCTGTTC CTGTCCAAGA GCCCTCTGGT GGACAAGTAC
GACCTATCCA CCCTGGCGGA GCTGTGCTGT GGAGCCGCTC CTCTGGCGAA
GGAGGTGGCC GAGATCGCCG TGAAGAGGCT GAACCTGCCA GGGATACGGT
GTGGCTACGG TCTAACAGAG TCTACCTCCG CCAACATCCA TACTCTGCAC
AACGAGTTCA AGTCCGGCTC CCTGGGCAAG GTGACACCTT ACATGGCCGC
CAAGATCATC GACAGGAACA CCGGCGAGGC CCTGGGTCCA AACCAGGTGG
GCGAGCTGTG CATCTGGGGA CCTATGGTAA CAAAAGGCTA TGTGAACAAC
CCACAGGCTA CTAAGGAGGC CATCGACGAC GACGGCTGGC TGCAC
``` gga gga ggc gga                                                        [lucN415]

ggatcc                                                                 [BamHI]

```
ATGGGCGTGC AGGTGGAGAC TATCTCCCCA GGAGACGGGC GCACCTTCCC
CAAGCGCGGC CAGACCTGCG TGGTGCACTA CACCGGGATG CTTGAAGATG
GAAAGAAATT TGATTCCTCC CGGGACAGAA ACAAGCCCTT TAAGTTTATG
CTAGGCAAGC AGGAGGTGAT CCGAGGCTGG GAAGAAGGGG TTGCCCAGAT
GAGTGTGGGT CAGAGAGCCA AACTGACTAT ATCTCCAGAT TATGCCTATG
GTGCCACTGG GCACCCAGGC ATCATCCCAC CACATGCCAC TCTCGTCTTC
GATGTGGAGC TTCTAAAACT GGAA                                 FKBB]
``` cgc tcg agt cta                                                        [XhoI]

Fig 1-4

(D) (SEQ ID No 8)

ggatcc [BamHI]

cccgggctgcaggaattct

ATGGTAGCCA TCCTCTGGCA TGAGATGTGG CATGAAGGTC TAGAAGAGGC
CTCTCGCTTG TACTTTGGGG AGAGGAACGT CAAAGGCATG TTTGAGGTGC
TGGAGCCCCT GCATGCTATG ATGGAACGCG GTCCCCAGAC CCTGAAGGAA
ACGTCCTTTA ATCAGGCATA TGGTCGAGAT TTAATGGAGG CACAAGAATG
GTGCCGAAAG TACATGAAAT CAGGGAACGT CAAGGACCTC ACCCAAGCCT
GGGACCTCTA CTATCACGTG TTCAGACGGA TATCA [FRB]

cgc tcg agt [XhoI]

gga ggc ggc gga

ACAAAAGGCT ATGTGAACAA CCCACAGGCT ACTAAGGAGG CCATCGACGA
CGACGGCTGG CTGCACTCTG GCGACTTCGG CTACTACGAC GAGGACGAGT
ATTTCTACAT CGTGGACCGG TACAAGGAGC TGATCAAATA CAAGGGCTAT
CAGGTCGCCC CTGTGGAGCT GGAGGAGATC CTCCTTCAGC ACCCAGGCAT
CAGGGACGTG GCCGTCGTGG GTATCCCTGA CATCGAGGCC GGCGAGCTGC
CAGCCGGCTT CGTGGTGAAG CAGCCCGGCG CCCAACTCAC CGCTAAGGAG
GTGTACGACT TCCTGGCCCA GAGGGTGTCT CACTCCAAGT ACCTGAGGGG
CGGCGTAAGG TTCGTGGACT CTATCCCCAG GAACGTGACA GGCAAGATTA
GTCGAAAAGA GCTGAGGGAG GCCCTGATGG AGAAGGCTTC TAAGCTG
[lucC394]

ggc ccg cgg ttc [SacII]

|  | Rap+ | DMSO | STDEV-R | STDEV-D |
|---|---|---|---|---|
| C394 N416 | 38,395 | 521 | 5,560 | 88 |
| C394 N415 | 41,131 | 454 | 8,481 | 104 |
| C394 N414 | 27,908 | 395 | 4,621 | 100 |
| C394 N413 | 36,746 | 329 | 6,660 | 57 |
| C394 N412 | 27,621 | 299 | 7,866 | 49 |

|  | Rap+ | DMSO | STDEV-R | STDEV-D |
|---|---|---|---|---|
| pTlunN-FKBP/pFRB-GlucC | 1,514 | 50 | 174 | 49 |
| plucN415-FKBP/pFRB-lucC394 | 50,740 | 302 | 7,418 | 247 |

Fig 9

| Gene name | Primer name | Primer sequence | SEQ ID No. | Template | Ligand | EC50 | T(min.) |
|---|---|---|---|---|---|---|---|
| SSTR2 | SSTR2_start_BamHI | ttggatccatgatggacatggcggatgagccac | 56 | TAKARA human brain cDNA | Somatostatin | $2 \times 10^{-8}$ | 12 |
| | SSTR2_R1107end_XhoI | tttctcgagccgatactggtttgaggtctccattg | 57 | | | | |
| EDNRB | ENDRB-nestF | tttaagcttatgcagccgcctcaagtct | 62 | GeneCopoeia clone | Endothelin 1 | $2 \times 10^{-8}$ | 8 |
| | EDNRB-nestR2 | ttctcgagccagatgagctgtatttattactggaacg | 63 | | | | |
| ADRB2 | ADRB2_start_BamHI | ttggatccatggggcaacccgggaacggca | 64 | TAKARA human brain cDNA | Isoproterenol | $3 \times 10^{-8}$ | 20 |
| | ADRB2_R1239end_XhoI | tttctcgagcccagccagcagtggtcatttgtactac | 65 | | | | |
| AGTRL1 | AGTRL1_start_BamHI | ttggatccatggaggaaggtggtgattttgac | 66 | TOYOBO human placental cDNA | [Pyr1]-apelin-13 | $5 \times 10^{-9}$ | 20 |
| | AGTRL1_R1140end_XhoI | tttctcgagccgtcaaccacaagggtctcctg | 67 | | | | |
| CCKBR | CCKBR_start_HindIII | tttaagcttatggagctgctaaagctgaacc | 68 | TAKARA human brain cDNA | gastrin-1 | $2 \times 10^{-9}$ | 20 |
| | CCKBR_R1548end_XhoI | ttttctcgagccgccagggccagtgtgctgat | 69 | | | | |

METHOD FOR HIGHLY SENSITIVE DETECTION OF PROTEIN-PROTEIN INTERACTION

CROSS-REFERENCE TO RELATED APPLICATIONS

This application is a U.S. national stage entry under 35 USC §371(b) of PCT International Application Serial No. PCT/JP2010/059160, filed May 28, 2010, which claims priority to Japanese Patent Application Serial Number 2009-131481, filed May 29, 2009 and Japanese Patent Application Serial Number 2010-037921, filed Feb. 23, 2010, the disclosures of all of which are hereby incorporated herein by reference.

TECHNICAL FIELD

This invention relates to methods for detecting a protein-protein interaction.

BACKGROUND ART

A method for detecting protein interaction between two target proteins by using complementarity of split luciferase fragments has been recently developed (Kim, S. B., Ozawa, T., Watanabe, S., Umezawa, Y., 2004. Proc. Natl. Acad. Sci. USA. 101, 11542-11547). The method for detecting a protein-protein interaction using complementarity is generally conducted by fusing fragments of a split reporter protein respectively with the target proteins, and in this process, each fragment does not have significant activity by itself. When the target proteins interact with each other, the inactive reporter protein fragments complement with each other to regain the activity which allows emission of the signal to enable indirect tracking of the protein-protein interaction.

Such method using the complementarity has been used for various reporter proteins such as dihydrofolate reductase and β-lactamase green fluorescent protein. Also, several luciferases such as *Renilla reniformis* luciferase, *Photinus Pyralis* luciferase, red-emitting *Photinus Pyralis* luciferase, and green-emitting *Photinus Pyralis* luciferase have been used.

SUMMARY OF INVENTION

Technical Problem

An object of the present invention is to provide an assay system using split luciferase which has remarkably high detection sensitivity.

Solution to Problem

The inventors of the present invention made an intensive study for solving the problem as described above, and found that, when using luciferase from Brazilian larval click-beetle (*Pyrearinus termitilluminans*), a C terminal fragment having SEQ ID NO: 1 and an N terminal fragment having any one of SEQ ID NOS: 2 to 6 are fused with each of the two interacting proteins respectively, and the two fusion proteins are bound, a luminescence with an intensity about 30 fold stronger than the conventional assay is emitted. The present invention has been completed on the bases of such a finding.

Accordingly, one aspect of the present invention is a fusion protein having the amino acid sequence of amino acid SEQ ID NO: 1. Another aspect of the present invention is a fusion protein having an amino acid sequence selected from the group consisting of amino acid SEQ ID NOS: 2 to 6.

In the present specification, the "protein has an amino acid sequence" means that the protein contains the amino acid sequence and that the protein may contain an amino acid sequence other than such an amino acid sequence. The "fusion protein" means a peptide derived from *Pyrearinus termitilluminans* luciferase (which, in the present invention, is a peptide consisting of an amino acid sequence selected from the group consisting of amino acid SEQ ID NO: 1 to 6) fused with a peptide not derived from *Pyrearinus termitilluminans* luciferase.

A further aspect of the invention is a complex of a fusion protein having the amino acid sequence of amino acid SEQ ID NO: 1 and a fusion protein having an amino acid sequence selected from the group consisting of amino acid SEQ ID NOS: 2 to 6.

A still further aspect of the invention is a DNA coding for an amino acid sequence selected from the group consisting of amino acid SEQ ID NOS: 1 to 6, or may be an expression vector that contains this DNA and is capable of expressing a fusion protein having an amino acid sequence selected from the group consisting of amino acid SEQ ID NOS: 1 to 6.

A still further aspect of the invention is a kit for detecting protein-protein interaction containing an expression vector for expressing a protein having a peptide comprising the amino acid sequence of amino acid SEQ ID NO: 1 and an expression vector for expressing a protein having a peptide comprising an amino acid sequence selected from the group consisting of amino acid SEQ ID NOS: 2 to 6.

A still further aspect of the invention is a method for detecting a fusion protein having the amino acid sequence of amino acid SEQ ID NO: 1, comprising the steps of allowing the fusion protein to interact with a binding fusion protein wherein the binding fusion protein has an amino acid sequence selected from the group consisting of amino acid SEQ ID NOS: 2 to 6 and is capable of binding with the fusion protein, to allow formation of a complex, and detecting luminescence emitted from the complex.

A still further aspect of the invention is a method for detecting a fusion protein containing an amino acid sequence selected from the group consisting of amino acid SEQ ID NOS: 2 to 6, comprising the steps of allowing the fusion protein to interact with a binding fusion protein wherein the binding fusion protein has the amino acid sequence of amino acid SEQ ID NO: 1 and is capable of binding with the fusion protein, to form a complex, and detecting luminescence emitted from the complex.

A still further aspect of the invention is a method for detecting a complex of a first fusion protein and a binding fusion protein being capable of binding with the first fusion protein, comprising the step of detecting luminescence emitted from the complex, wherein the first fusion protein has the amino acid sequence of amino acid SEQ ID NO: 1 and the binding fusion protein has an amino acid sequence selected from the group consisting of amino acid SEQ ID NOS: 2 to 6.

A still further aspect of the invention is a method for detecting binding of first and second fusion proteins which are bound to each other, wherein the first fusion protein has the amino acid sequence of amino acid SEQ ID NO: 1 and the second fusion protein has an amino acid sequence selected from the group consisting of amino acid SEQ ID NOS: 2 to 6, comprising the steps of allowing the first fusion protein to interact with the second fusion protein to allow formation of a complex, and detecting luminescence emitted from the complex. This method may further comprise the steps of fusing the amino acid sequence of amino acid SEQ ID NO: 1 with a first protein to prepare the first fusion protein, and fusing an amino acid sequence selected from the group consisting of amino acid SEQ ID NOS: 2 to 6 with a second protein to prepare the second fusion protein.

A still further aspect of the invention is a method for screening a fusion protein library for a binding fusion protein being capable of binding to a first fusion protein, comprising the steps of allowing the first fusion protein to interact with a plurality of second fusion proteins, wherein the first fusion protein has the amino acid sequence of amino acid SEQ ID NO: 1 and the second fusion proteins have an amino acid sequence selected from the group consisting of amino acid SEQ ID NOS: 2 to 6 and are in the fusion protein library, and identifying the binding fusion protein that forms a complex with the first fusion protein by detecting luminescence emitted by the complex.

A still further aspect of the invention is a method for screening for a binding fusion protein being capable of binding with a first fusion protein comprising the steps of allowing the first fusion protein to interact with a plurality of second fusion proteins, wherein the first fusion protein has an amino acid sequence selected from the group consisting of amino acid SEQ ID NOS: 2 to 6, and the second fusion proteins have the amino acid sequence of amino acid SEQ ID NO: 1, and identifying the binding fusion protein that forms a complex with the first fusion protein detecting luminescence emitted from the complex.

BRIEF DESCRIPTION OF DRAWINGS

FIG. 1A is the nucleotide sequence of the cDNA of *Pyrearinus termitilluminans* luciferase.

FIG. 1B is a list of PCR primers used in preparing plucN and plucC in one example of the present invention.

FIG. 1C is the nucleotide sequence of the DNA inserted in multicloning site of pcDNA3.1 in pcDNA3.1/myc-His(B).

FIG. 1D is the nucleotide sequence of the DNA inserted in multicloning site of pcDNA4 in pcDNA4/V5-His(B).

FIG. 2-2 is graphs showing the results of the luminescence intensity measurement in a luciferase split assay in one Example of the present invention, which were obtained by using combinations of pFRB-lucC392 to pFRB-lucC394 and plucN404-FKBP to plucN417-FKBP. For each sample in the bar graph, the left bar is the result for the rapamycin-containing culture medium, and the right bar is the result for the DMSO-containing culture medium.

FIG. 3-1 is graphs showing the results of the luminescence intensity measurement in a luciferase split assay in one Example of the present invention, which were obtained by using combinations of pFRB-lucC394 to pFRB-lucC399 and plucN404-FKBP to plucN417-FKBP. For each sample in the bar graph, the left bar is the result for the rapamycin-containing culture medium, and the right bar is the result for the DMSO-containing culture medium.

FIG. 3-2 is graphs showing the results of the luminescence intensity measurement in a luciferase split assay in one Example of the present invention, which were obtained by using combinations of pFRB-lucC400 to pFRB-lucC403 and plucN404-FKBP to plucN417-FKBP. For each sample in the bar graph, the left bar is the result for the rapamycin-containing culture medium, and the right bar is the result for the DMSO-containing culture medium.

FIG. 3-3 is graphs showing the results of the luminescence intensity measurement in a luciferase split assay in one Example of the present invention, which were obtained by using combinations of pFRB-lucC404 to pFRB-lucC407 and plucN404-FKBP to plucN417-FKBP. For each sample in the bar graph, the left bar is the result for the rapamycin-containing culture medium, and the right bar is the result for the DMSO-containing culture medium.

FIG. 9 is a table showing names of the GPCRs used, PCR templates and primer sequences used in preparing the expression vectors for expressing fusion proteins, ligands used for the stimulation, ligand concentrations (EC50) at which the luminescence was detected (unit: molar concentration), and the times (T) of the maximum luminescence observation after the stimulation, in the experiment conducted for the GPCRs.

DESCRIPTION OF EMBODIMENTS

Figures 1, 2:
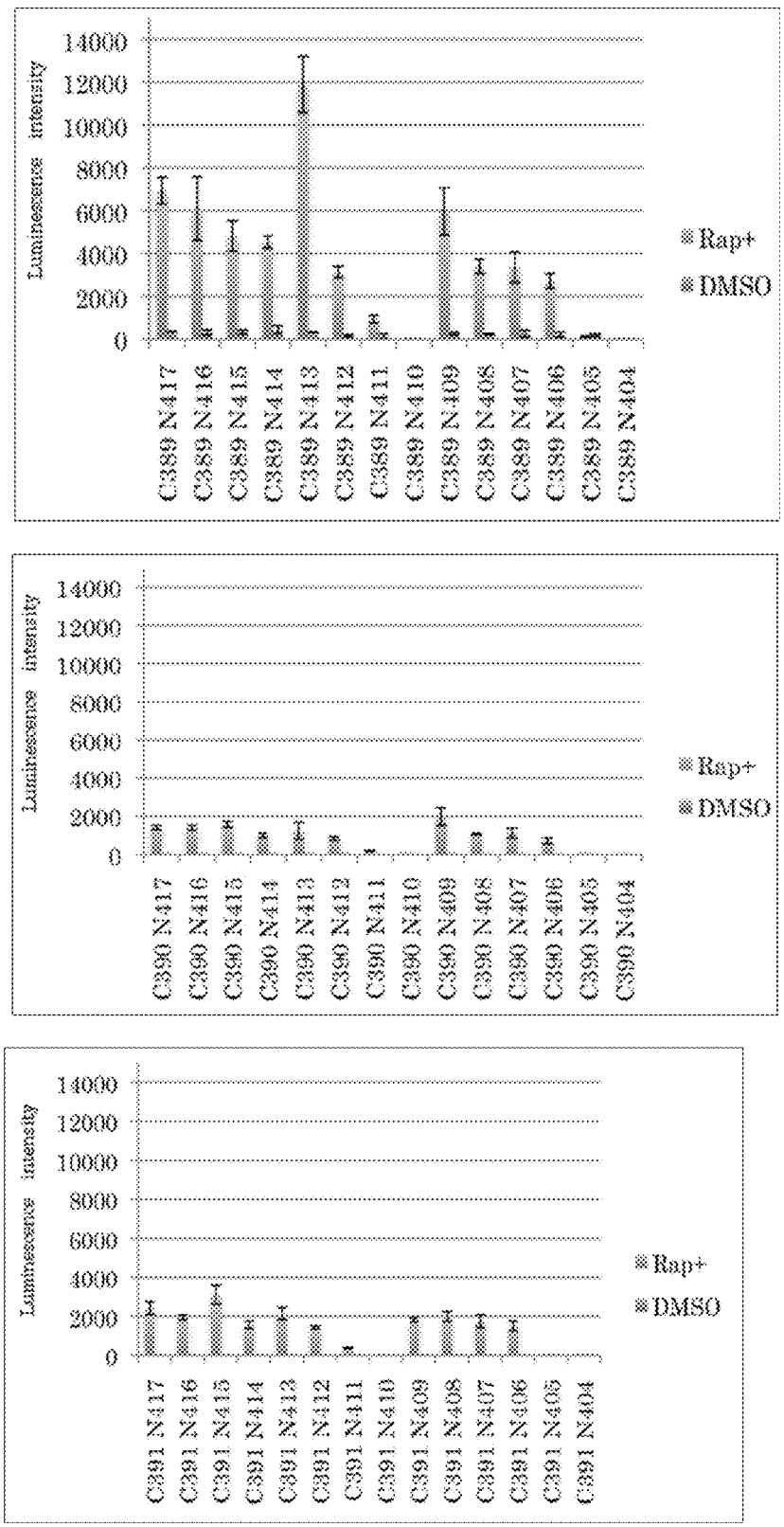
FIG. 2-1 is graphs showing the results of the luminescence intensity measurement in a luciferase split assay in one Example of the present invention, which were obtained by using combinations of pFRB-lucC389 to pFRB-lucC391 and plucN404-FKBP to plucN417-FKBP. For each sample, the left bar of the bar graph is the result for the rapamycin-containing culture medium, and the right bar is the result for the DMSO-containing culture medium.
Figure 2:
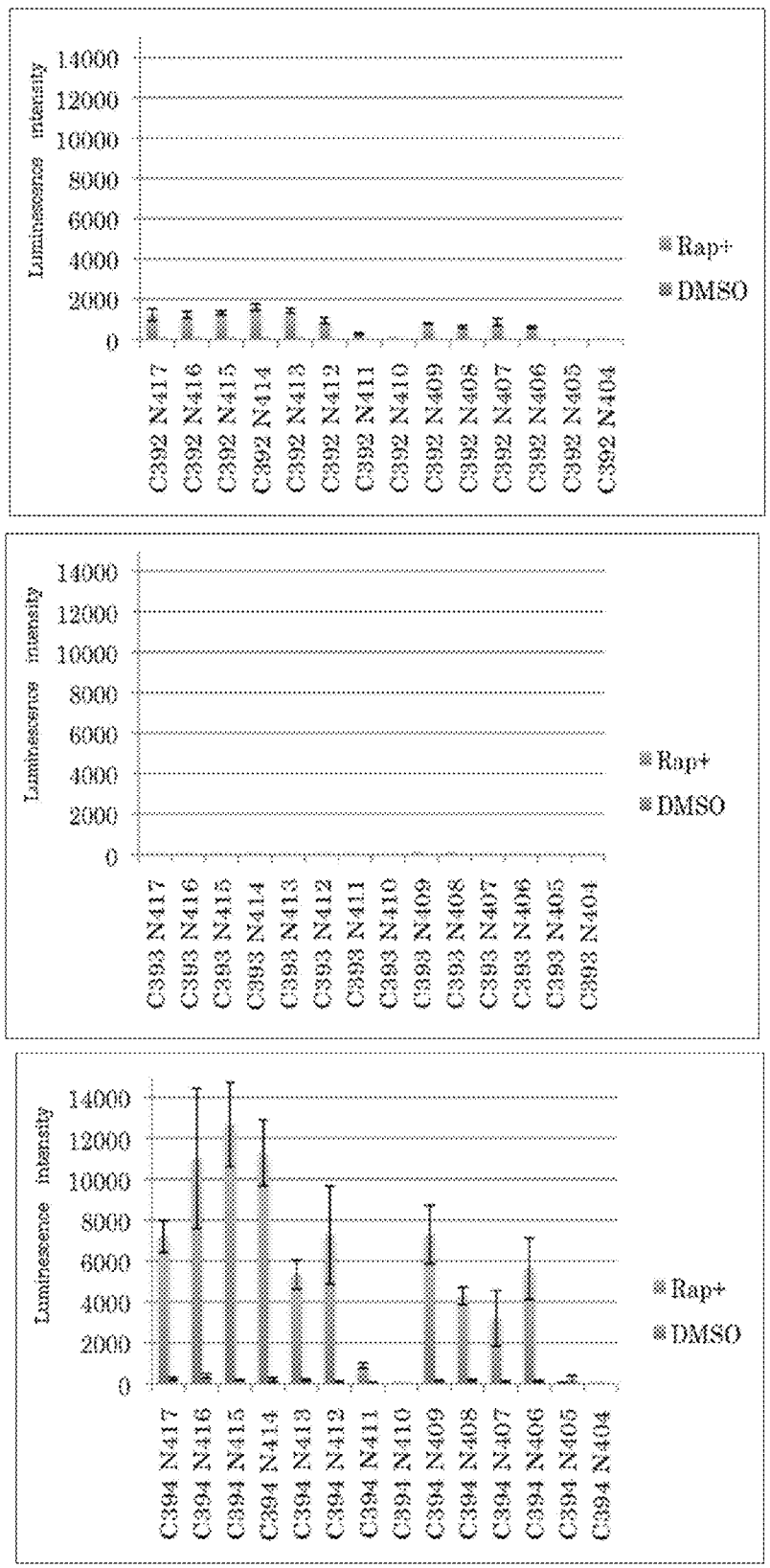

Next, embodiments of the present invention completed based on the finding as described above are described in detail by referring to Examples. Unless otherwise noted, methods described in standard protocols such as J. Sambrook, E. F. Fritsch & T. Maniatis (Ed.), Molecular cloning, a laboratory manual (3rd edition), Cold Spring Harbor Press, Cold Spring Harbor, N.Y. (2001); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd. as well as their modifications and improvements are used in the embodiments and Examples. When commercially available reagent, kit and assay apparatus are used, protocols attached thereto are used unless otherwise noted.

The objects, features, advantages, and ideas of the present invention are clear for those skilled in the art from the description of the invention, and those skilled in the art will be readily capable of reproducing the invention. The embodiments and Examples as described below are preferable embodiments of the present invention, which are presented for the purpose of illustration and explanation, and the present invention is not limited by these embodiments and Examples. It is clear for those skilled in the art that the description of the present invention can be modified in various ways within the scope and intention of the invention herein described.

[Principle]

The present invention provides a luciferase split assay system with a high detection sensitivity. In this assay system, an amino acid sequence comprising amino acid SEQ ID NO: 1 and an amino acid sequence selected from the group consisting of amino acid SEQ ID NOS: 2 to 6 from *Pyrearinus termitilluminans* luciferase whose sequence is described in FIG. 1A, are used. Next, methods using this assay system are described in detail. The luciferase split assay is a technique known in the art, and the procedure not described in this specification may be conducted according to common knowledge of those skilled in the art.

First, a first protein (referred to as a first fusion protein) having the amino acid sequence of amino acid SEQ ID NO: 1 (this peptide moiety is referred to as lucCmax) and a second protein (referred to as a second fusion protein) having an amino acid sequence (this peptide moiety is referred to as lucNmax) selected from the group consisting of amino acid SEQ ID NOS: 2 to 6 are synthesized. It should be noted that the first protein and the second protein can bind to each other under particular conditions.

While the fusion proteins can be chemically synthesized for use in the assay system, the fusion proteins may be provided by constructing expression vectors coding for the fusion proteins and expressing the fusion proteins in the assay system, as will be described below. In such a case, the fusion proteins may be expressed either transiently or permanently. The former is preferable when the assay system is an in vitro system, and the latter is preferable when the assay system is an in vivo system such as a cell. In each fusion protein, the lucCmax or the lucNmax may be connected to the protein either directly or via a linker. The linker is preferably a peptide moiety with an adequate length.

When both of the fusion proteins are introduced in the assay system, the first protein and the second protein bind to each other, and as a consequence, the lucCmax and the lucNmax will be located at positions capable of undergoing an interaction, and the lucCmax and the lucNmax will reconstitute the luciferase to recover luciferase activity so that the luciferase is capable of emitting light under adequate luminescent conditions. The luciferase activity may be measured, when the assay system is a cell, by adding luciferin to the cell culture, and preparing a cell extract to measure the luciferase activity. In this case, the activity is readily measurable by using a commercially available Emerald Luc Luciferase Assay Reagent/Lysis Solution (TOYOBO) or the like.

In this assay system, a luminescence intensity that is about 30 times or more stronger than the conventional assay is realized when the amino acid sequence of the lucC is amino acid SEQ ID NO: 1 and the amino acid sequence of the lucN is an amino acid sequence selected from the group consisting of amino acid SEQ ID NOS: 2 to 6.

[Construction of Expression Vectors]

As described above, the introduction of the fusion proteins into the assay system can be realized by constructing expression vectors coding for the fusion proteins and expressing the fusion proteins in the assay system.

The expression vectors coding for the fusion proteins can be readily constructed by constructing vectors containing DNA coding for the amino acid sequence selected from the group consisting of amino acid SEQ ID NO: 1 to 6 in advance.

For example, such a vector may be constructed to have DNA coding for the lucNmax having the initiation codon ATG inserted downstream of an expression promoter which can function in the assay system and followed by a multicloning site immediately downstream and a transcription termination signal further downstream. When DNA coding for the intended protein is inserted in frame in the multicloning site, expression of the fusion protein of the lucNmax and the intended protein is facilitated.

Another exemplary vector has a form comprising an expression promoter that can function in the assay system, the initiation codon ATG, DNA coding for the multicloning site and the lucCmax, and the transcription termination signal in this order. When DNA coding for the intended protein is inserted in frame in the multicloning site, expression of the fusion protein of the lucCmax and the intended protein is facilitated.

Furthermore, an expression vector for the fusion protein having lucCmax or lucNmax can be readily constructed for the purpose of, for example, detecting a protein-protein interaction when a kit containing a vector having DNA coding for the amino acid sequence of the amino acid SEQ ID NO: 1, namely, the lucCmax and a vector having DNA coding for an amino acid sequence selected from the group consisting of amino acid SEQ ID NOS: 2 to 6, namely, the lucNmax is prepared.

[Use of the Assay System]

Next, exemplary uses of the assay system of the present invention are described.

First of all, a fusion protein having lucCmax can be detected. For example, when a first fusion protein that has been made by fusing a target protein to be detected with lucCmax exists in the assay system, a second fusion protein that has been made by fusing a binding protein that binds to the target protein with lucNmax is prepared as a probe and is introduced in the assay system. Then, the binding protein in the second fusion protein should bind to the target protein in the first fusion protein; thereby the lucCmax and the lucNmax interact and gain luciferase activity. By detecting the luciferase activity, the target fusion protein having the lucCmax can be detected. Specifically, an expression vector expressing the first fusion protein is prepared and introduced in a cell. Next, an expression vector expressing the second fusion protein is prepared and introduced in the cell expressing the first fusion protein. Then the fusion protein having the lucCmax is detected by measuring the luciferase activity as described above.

Next, a fusion protein having lucNmax can be detected. For example, if a first fusion protein that has been made by fusing the target protein to be detected with lucNmax exists in the assay system, a second fusion protein that has been made by fusing a binding peptide that binds to the target protein with lucCmax is prepared as a probe and is introduced in the assay system. Then, the binding peptide in the second fusion protein will bind to the target peptide in the first fusion protein; thereby the lucNmax and the lucCmax interact and gain luciferase activity. By detecting the luciferase activity, the target fusion protein having the lucNmax can be detected. Specifically, an expression vector expressing the first fusion protein is prepared and introduced in a cell. Next, an expression vector expressing the second fusion protein is prepared, and introduced in the cell expressing the first fusion protein. Then the fusion protein having the lucNmax is detected by measuring the luciferase activity as described above.

Further, a complex of a fusion protein having the lucNmax and a fusion protein having the lucCmax can be detected. When these fusion proteins form a complex, the lucNmax and the lucCmax interact and gain luciferase activity. By detecting the luciferase activity, the complex can be detected. For detection, the assay system including the complex may be placed under the conditions wherein the luciferase activity can be detected. When the assay system is a cell, the luciferase activity may be measured by the procedure as described above.

Further, binding of the first and second proteins that have mutual binding ability can be detected, because a first fusion protein and a second fusion protein are synthesized by fusing a first protein and a second protein with the lucNmax and the lucCmax in advance respectively so that the luciferase activity will be detectable if the first fusion protein binds to the second fusion protein. It can be examined whether the first protein can bind to the second protein by using this method; when the first fusion protein prepared by fusing the lucNmax with the first protein and the second fusion protein prepared by fusing the lucCmax with the second peptide are introduced in the assay system, the luciferase activity will be detected if the first protein binds with the second protein and the luciferase activity will not be detected if the first protein does not bind with the second protein. Specifically, expression vectors expressing the first fusion protein or the second fusion protein are separately prepared and both of them are introduced in the same cell, and then, if luminescence from the luciferase reconstituted in the cell is observed by measuring the luciferase activity as described above, the first protein and the second protein can be judged to be bound each other, and the first protein and the second protein can be judged not to be bound if no luminescence is detected.

Further, it is possible to screen a protein library for a binding protein that is capable of binding to a first protein. More specifically, a first fusion protein is prepared by fusing a first protein with lucNmax or lucCmax, and second fusion proteins are prepared by fusing second proteins in the protein library with lucCmax or lucNmax, respectively; and when the first fusion protein and the second fusion proteins are allowed to interact with each other, only the second fusion proteins having the binding proteins capable of binding with the first protein form complexes with the first fusion protein. Accordingly, the second proteins that bind to the first protein can be identified by detecting luminescence emitted from the complexes. Specifically, a cell transformed with an expression vector which expresses a first fusion protein comprising a first protein fused with lucNmax is prepared, and a cDNA library which has been constructed to express proteins in the form fused with lucCmax is introduced in the cell; then, luciferin is added to the culture medium, and luminescent cells are identified and cloned. DNAs derived from the library are recovered from the clones, and the genes expressed are identified to thereby obtain cDNAs of the second proteins that form the complexes with the first protein.

EXAMPLES

Example 1

In this Example, interacting proteins, FKBP (NM_054014) and FRB (NM_019906), which are bound each other in the presence of rapamycin, were fused with lucNs, peptides having the N terminal sequence of *Pyrearinus termitilluminans* luciferasem and lucCs, peptides having the C terminal sequence of *Pyrearinus termitilluminans* luciferase, respectively. It will be shown that the luminescence activity of the complex of the interacting proteins varies according to the combination of lucN and lucC, and is remarkably enhanced when lucNmax (SEQ ID NO: 2 to 6; the amino acid sequence of 1st-412nd to 416th amino acid residues) is used in combination with lucCmax (SEQ ID NO: 1; the amino acid sequence of 394th-542nd amino acid residues).

First, PCR was conducted using a cDNA of *Pyrearinus termitilluminans* luciferase, whose sequence is shown in FIG. 1A, as template and using the primers of FIG. 1B to obtain 14 kinds of DNA fragments coding for 14 kinds of peptide each having an amino acid sequence from N terminal amino acid residue to the 404th to 417th amino acid residues, which were obtained by using the pair of N-PtGR-F001 and N-PtGR-R404 to R417, and 25 kinds of DNA fragments coding for amino acid sequences from C terminal amino acid residue to the 389th to 413rd amino acid residues, which were obtained by using C-PtGR-R542 and C-PtGR-F389 to F413. The DNA coding for the N terminal region was cleaved with HindIII and BamHI, pFKBP was cleaved with BamHI and XhoI, and pcDNA3.1/myc-His (B) was cleaved with HindIII and XhoI to conduct three molecule ligation and thus 14 kinds of plucN-FKBP were prepared. In the meanwhile, the DNA coding for the C terminal region was cleaved with XhoI and SacII, pFRB was cleaved with BamHI and XhoI, and pcDNA4/V5-His (B) was cleaved with BamHI and SacII to conduct three molecule ligation and thus 25 kinds of pFRB-lucC were prepared. pcDNA3.1/myc-His (B) and pcDNA4/V5-His (B) are plasmid vectors having the sequence of SEQUENCE ID NOS: 7 and 8 inserted therein, respectively. The nucleotide sequence of the DNA inserted in the multi-cloning site of pcDNA3.1 is shown in FIG. 1C and the nucleotide sequence of the DNA inserted in the multicloning site of pcDNA4 is shown in FIG. 1D.

For the 339 cases where the luciferase was reconstructed as the amino acid sequence of the original luciferase (overlapping of the amino acid: 0), or with partial overlapping (overlapping of the amino acid: 1 or more) in the combinations of 14 kinds of plucN-FKBP and 25 kinds of pFRB-lucC, each pair of the expression vectors was transfected to COST cells on a 96 well plastic culture dish using TtansIT Transfection Reagents (TAKARA). After about 16 hours from the transfection, the culture medium was replaced with the medium containing 1 μm of rapamycin; after 24 hours of incubation, ELA (TOYOBO) was added and the luminescence was measured by TriStar LB941 (Berthold Technologies).

Figures 1, 3:
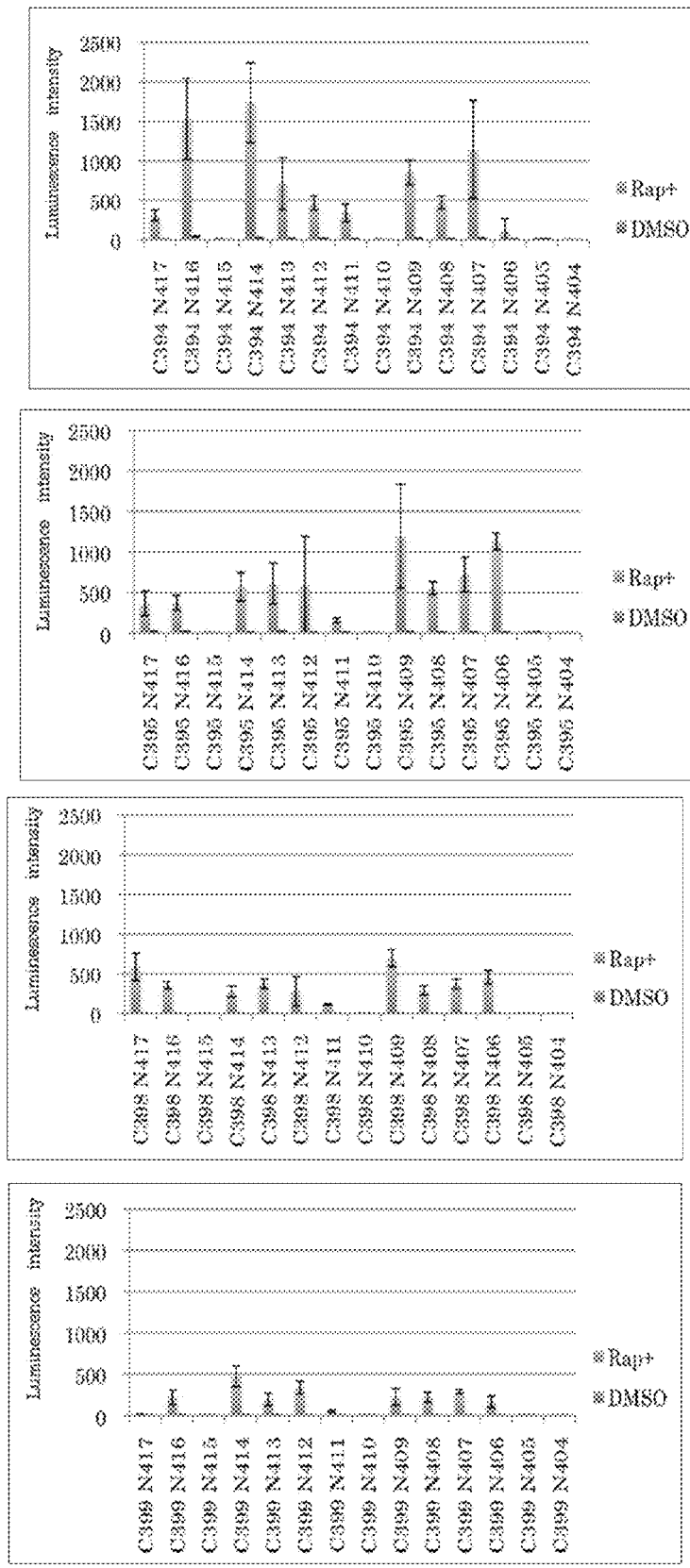
Figures 2, 3:
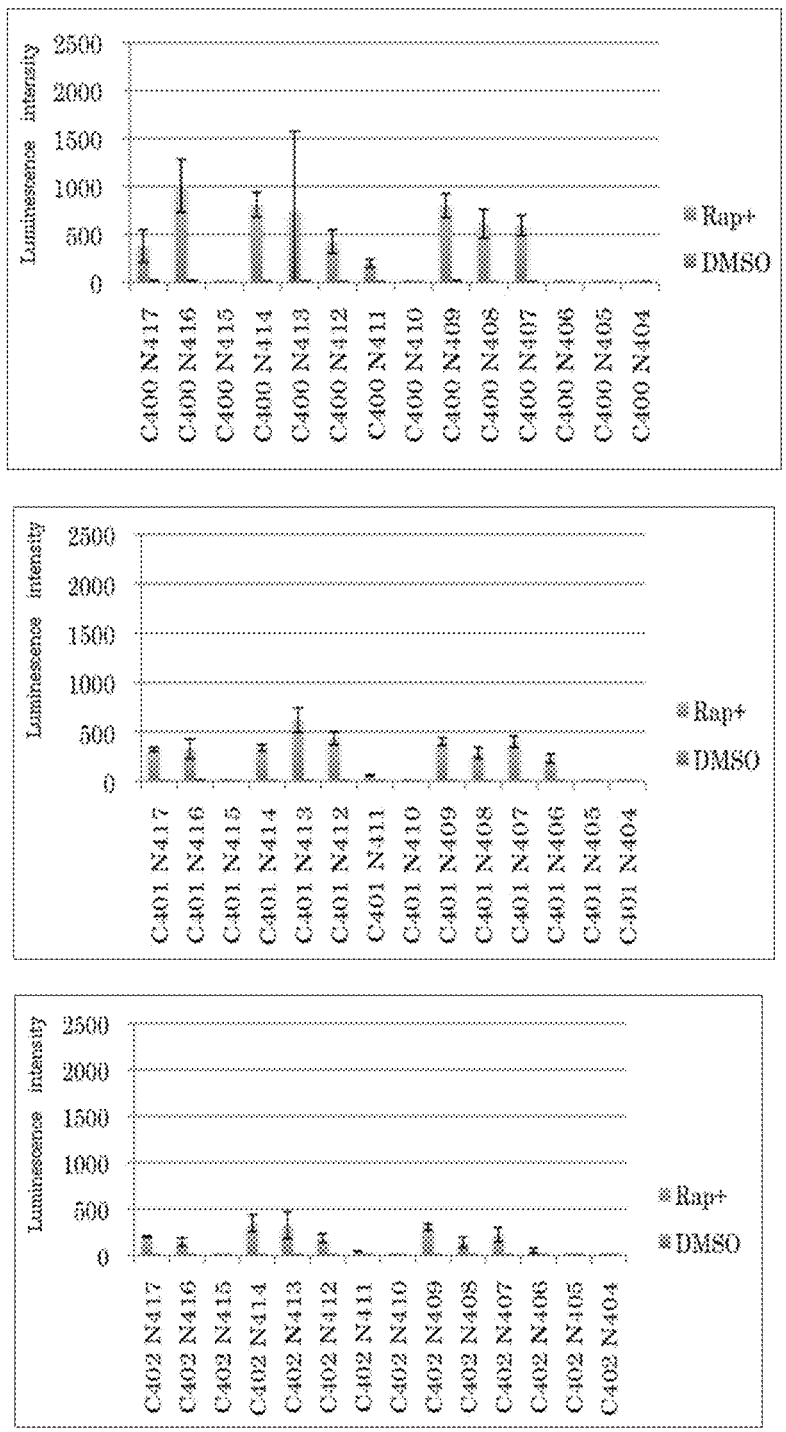
Figures 2, 3:
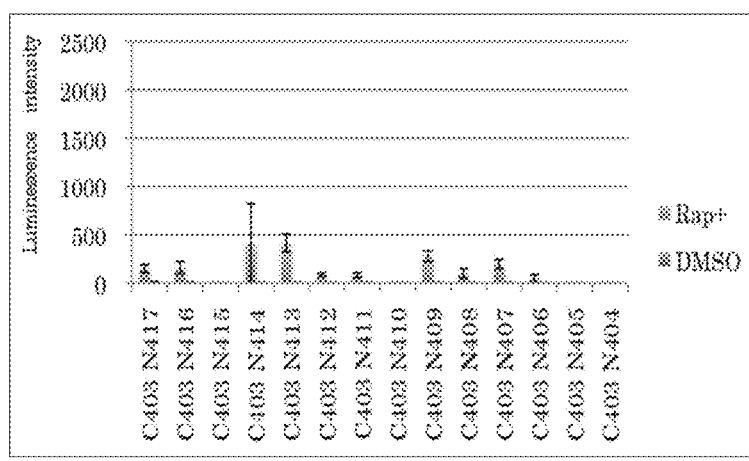
Figure 3:
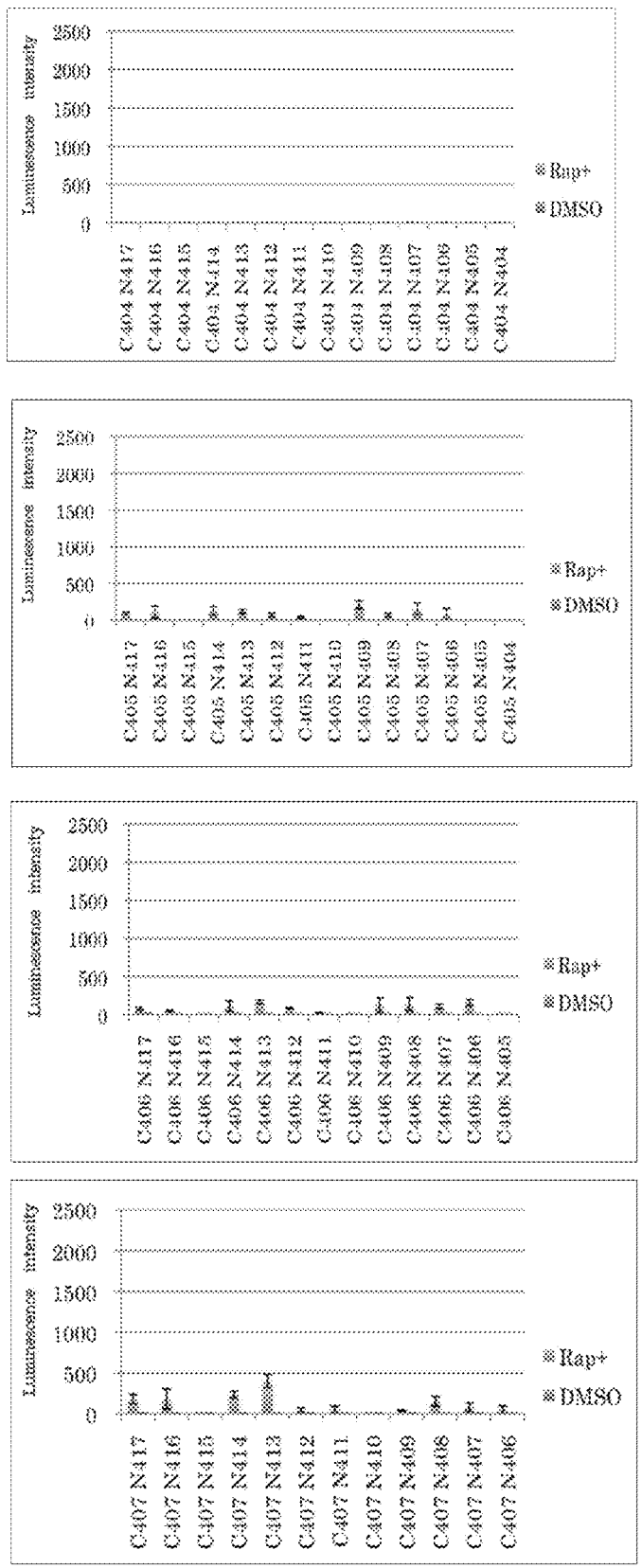

As shown in FIGS. 2 and 3, high levels of signal were obtained for pFRB-lucC394, and the signal was the highest in the case of plucN412-FKBP to plucN416-FKBP. It should be noted that almost no signal was obtained for pFRB-lucC408 to pFRB-lucC413, and these cases are not shown in the drawings. Further, in FIG. 3, no signal was obtained in the case of plucN415-FKBP due to the experimental failure.

Figures 4, 5:
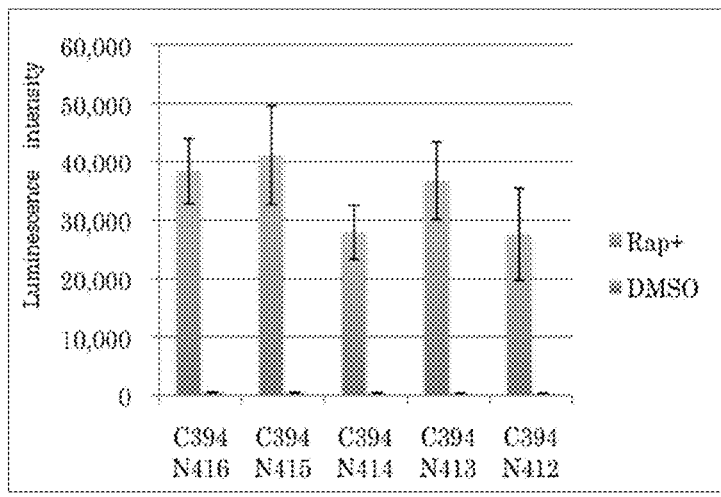
FIG. 4 is a graph and a table showing the results of the luminescence intensity measurement in a luciferase split assay in one Example of the present invention, which were obtained by using combinations of pFRB-lucC394 and plucN412-FKBP to plucN416-FKBP. In the table, Rap+ is the luminescence intensity when binding was induced; DMSO is the luminescence intensity when binding was not induced (namely, the background); STDEV-R is the standard deviation when binding was induced with Rap+; and STDEV-D is the standard deviation when binding was not induced with DMSO. For each sample in the graph, the left bar is the result for the rapamycin-containing culture medium, and the right bar is the result for the DMSO-containing culture medium.
FIG. 5 is a table showing the results of the luminescence intensity measurement in a luciferase split assay in one Example of the present invention, which were obtained by using combination of plucN415-FKBP and pFRB-lucC394 and conventional combination of pTlucN-FKBP and pFRB-GlucC. Symbols are as defined above for FIG. 4.

Accordingly, the experiment was conducted again for plucN412-FKBP to plucN416-FKBP, and as shown in FIG. 4, the highest signals were obtained for plucN412-FKBP to plucN416-FKBP at almost the same level.

The luminescence intensity obtained by using the combination of plucN415-FKBP and pFRB-lucC394 which was shown to be the most suitable was compared with the luminescence intensity obtained by the combination of pTlucN-FKBP and pFRB-GlucC which had been accepted as the most suitable combination. pTlucN-FKBP is a vector constructed by amplifying an N terminal fragment of the cDNA of red-emitting Photinus Pyralis luciferase by PCR using the primers as shown below and constructing the vector in the same manner as plucN-FKBP, and pFRB-GlucC is a vector constructed by amplifying a C terminal fragment of the cDNA of green-emitting Photinus Pyralis luciferase by PCR using the primers as shown below and constructing the vector in the same manner as pFRB-lucC.

```
(TlucN-1)
                                              (SEQ ID No. 9)
5'AAGCTTGCCATGGTAAAGCGTGAGAAAAATGTC 3'

(TlucN-2)
                                              (SEQ ID No. 10)
5'GGATCCTCCGCCTCCTCCGCCGTCGTCGATGGCCTC 3'

(GlucC-1)
                                              (SEQ ID No. 11)
5'aggCTCGAGTGGAGGCGGCGGAGGCTGGCTGCACTCTGGCGACTTC
3'

(GlucC-2)
                                              (SEQ ID No. 12)
5'cgcGGGCCCAGCTTAGAAGCCTTCTCCATCAGGGC 3'
```

As shown in FIG. 5, the luminescence intensity obtained by the combination of plucN415-FKBP and pFRB-lucC394 was about 30 fold higher than the conventional combination of plucN415-FKBP and pFRB-lucC394. Thus, the luminescence intensity about 30 fold higher than the conventional luminescence intensity was realized by using the *Pyrearinus termitilluminans* luciferase and conducting the luciferase split assay by using the C terminal fragment lucC394 and the N terminal fragments lucN412 to lucN416.

Example 2

In this Example, somatostatin receptor (SSTR2; somatostatin type 2 receptor) (NM_000794) which is a GPCR (G-protein coupled receptor) and β-arrestin (arrestin, beta 2) (NM_004313) were used instead of the FKBP and FRB. SSTR2 is a membrane protein on the cell membrane, and when somatostatin binds to extracellular domain of the GPCR, the intracellular domain of the SSTR2 binds to β-arrestin that is an adapter molecule in the cytoplasm, and a signal is transduced downstream. Accordingly, the C terminal of the SSTR2 was bonded to the C terminal of the Eluc, and the N terminal of the β-arrestin was bonded to N terminal of the Eluc, and the fusion proteins were expressed in the cultured cells, and somatostatin was added to the cultured cells to examine luminescence from the cells.

First, PCR was conducted by using a human brain cDNA library (TAKARA) as template with the primers as shown below to obtain DNA fragments coding for arrestin and the SSTR2.

```
ARRB2-nestF2:
                                              (SEQ ID NO: 54)
AAAGGATCCATGGGGGAGAAACCCGGGACCAGGGTCT ARRB2-nestR-Eco:
                                              (SEQ ID NO: 55)
AAGAATTCCAGCAGAGTTGATCATCATAGT SSTR2_start_Bam:
                                              (SEQ ID NO: 56)
TTGGATCCATGGACATGGCGGATGAGCCAC
```

-continued
```
SSTR2_R1107end_XhoI:
                                              (SEQ ID NO: 57)
TTTCTCGAGCCGATACTGGTTTGGAGGTCTCCATTG
```

The DNA coding for the arrestin was cleaved with BamHI and EcoRI, and ligated to the plucN415 that had been cleaved with BamHI and EcoRI and plucN415-arrestin was obtained. The plucN415 used had been obtained by cleaving the plucN415-FKBP in Example 1 with HindIII and BamHI and ligating with pcDNA3.1/myc-His(B) cleaved with HindIII and BamHI.

In the meanwhile, the DNA fragment coding for the SSTR2 was cleaved with BamHI and XhoI, inserted in the multicloning site of pcDNA4/V5-His(B), and pSSTR2 was obtained. Then, the DNA coding for lucC394 with the linker whose length was extended to 22 amino acids was cleaved with XhoI and SacII, inserted at XhoI-SacII site of the pSSTR2 and pSSTR2-lucC394 was obtained. It is to be noted that the linker length of the lucC394 was extended to 22 amino acids step by step by conducting PCR using pFRB-lucC394 as template and linker C12-F-XhoI (SEQ ID NO: 58) and PtGR-R542-SacII (SEQ ID NO: 61) as primers, cleaving the PCR product with XhoI and SacII, and inserting the fragment at the XhoI-SacII site of the pSSTR2; conducting PCR using this producer as template and linker C17-F-XhoI (SEQ ID NO: 59) and PtGR-R542-SacII (SEQ ID NO: 61) as primers, cleaving the PCR product with XhoI and SacII, and inserting the fragment at XhoI-SacII site of the pSSTR2; and finally, conducting PCR using this product as template and linker C22-F-XhoI (SEQ ID NO: 60) and PtGR-R542-SacII (SEQ ID NO: 61) as primers, cleaving the PCR product with XhoI and SacII, and inserting the fragment at XhoI-SacII site of the pSSTR2.

```
linkerC12-F-XhoI:
                                              (SEQ ID NO: 58)
AGGCTCGAGTGGCGGTGGAGGTAGTGGAGGCGGCGGAACAAA linkerC17-F-XhoI:
                                              (SEQ ID NO: 59)
AGGCTCGAGTGGTGGTGGGGGCAGTGGCGGTGGAGGTAGTGG linkerC22-F-XhoI:
                                              (SEQ ID No. 60)
AGGCTCGAGTGGAGGTGGCGGTTCTGGTGGTGGGGGCAGTGGCGGT PtGR-R542-SacII:
                                              (SEQ ID No. 61)
TTTCCGCGGCAGCTTAGAAGCCTTCTC
```

Figure 6:
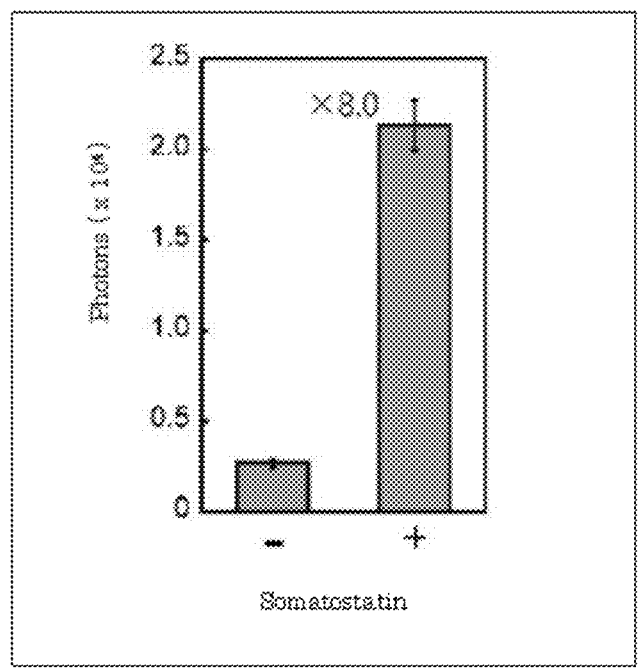
FIG. 6 is a graph showing the results of the comparison of the luminescence intensity, in one Example of the present invention, for the cases when somatostatin was added and not added to HEK293 cells in which pSSTR2-lucC394 and plucN415-arrestin had been introduced to transiently express SSTR2-lucC394 and lucN415-arrestin, respectively. x axis shows presence (+) and absence (−) of the somatostatin, and y axis shows number of photons ($\times 10^4$).

The pSSTR2-lucC394 and plucN415-arrestin thus prepared were transfected to the HEK293 cells cultured in a 96 well plastic culture dishes by using TtansIT Transfection Reagents (TAKARA). After about 40 hours from the transfection, the cells were incubated in a culture medium containing 1 μm of somatostatin for 12 minutes, ELA (TOYOBO) was added, and the luminescence was measured with TriStar LB941 (Berthold Technologies). The luminescence was also measured for the control cell with no addition of the somatostatin, and the results were compared. As shown in FIG. 6, addition of the somatostatin resulted in the significant enhancement of the luminescence, whose intensity was eight times.

Next, HEK293 cells which had been transfected with plucN415-arrestin using 6 cm plastic culture dishes as described above were cultured for 20 days in a culture medium containing 0.8 mg/mL of G418 and an HEK293 cell line (HEK293-ARRB2) capable of constantly expressing lucN415-arrestin was prepared. This cell line was transfected with pSSTR2-lucC394 as described above, and the cells were cultured for 20 days in a culture medium containing 0.8 mg/mL of G418 and 0.04 mg/mL of Zeocin and an HEK293 cell line (HEK293-ARRB2-SSTR2) capable of constantly expressing lucN415-arrestin and SSTR2-lucC394 was prepared.

The cells were cultured in a 96 well plastic culture dish, and after stimulating the cells for 12 minutes with somatostatin or its analog (RIM23052 or BIM23056) at various concentrations, luminescence was measured as described above. A dose-response curve showing relationship of the luminescence intensity and the ligand concentration was made from the results obtained.

Figure 7:
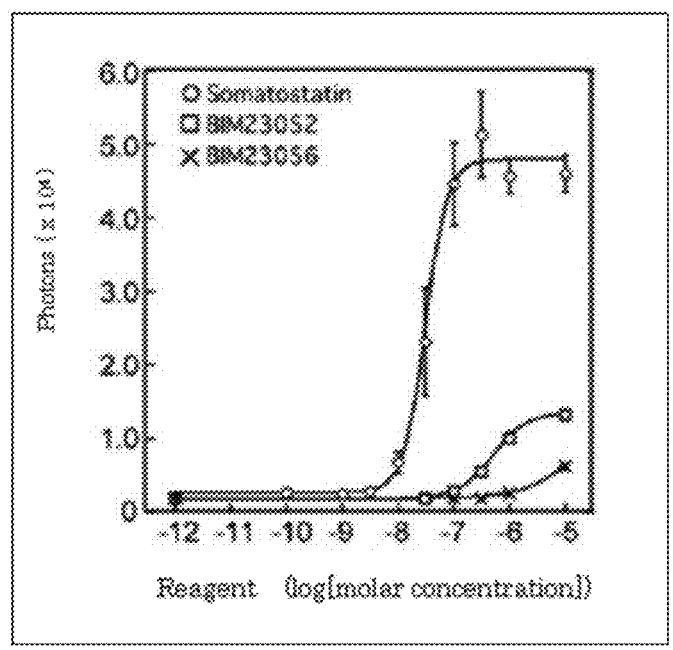
FIG. 7 is a graph showing dose-response curves in one Example of the present invention, when HEK293-ARRB2-SSTR2 cell line was stimulated with somatostatin or its analogs (RIM23052 or BIM23056) at various concentrations. x axis shows concentration of each reagent (log [molar concentration]), and y axis shows number of photons ($\times 10^4$).

As shown in FIG. 7, in the case of somatostatin, enhancement in the luminescence was observed at a concentration of $3 \times 10^{-9}$ to $3 \times 10^{-7}$ M, and the enhancement was not enhanced at the higher somatostatin concentration. In the case of the somatostatin analogues, such enhancement in the luminescence was not observed at the same concentration. Thus, quantitative assay of the ligand activity to the receptor was enabled using the assay system in which the luciferase split assay of the present invention is applied to the receptor and the intracellular binding element.

Figure 8:
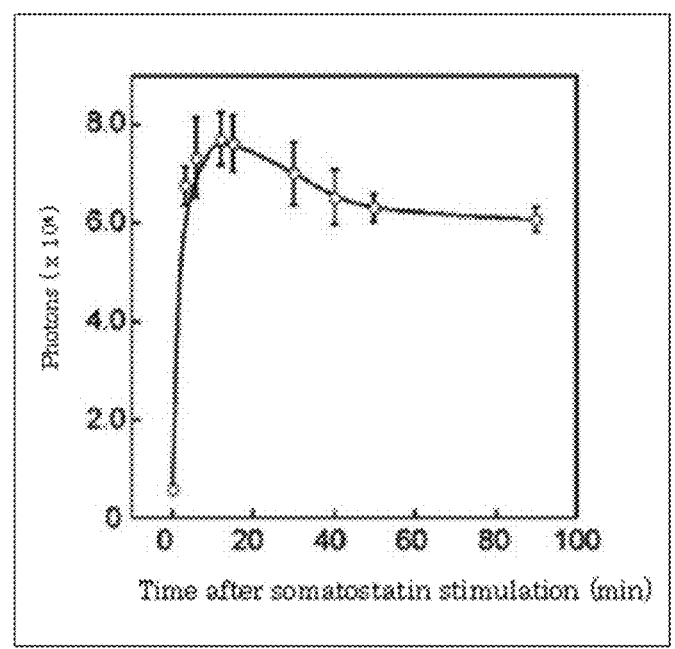
FIG. 8 is a graph showing a time-response curve in one Example of the present invention, when HEK293-ARRB2-SSTR2 cell line was stimulated with $1 \times 10^{-6}$ M of somatostatin, and luminescence was measured with time. x axis shows time (min), and y axis shows number of photons ($\times 10^4$).

When HEK293-ARRB2-SSTR2 was stimulated with $1 \times 10^{-6}$ M somatostatin and the luminescence was measured at 3 minutes, 6 minutes, 12 minutes, 15 minutes, 30 minutes, 40 minutes, 50 minutes, and 90 minutes after the stimulation, the luminescence reached 90% of the maximum luminescence in 5 minutes and the luminescence reached its maximum in 12 minutes, as shown in FIG. 8. After 12 minutes, the luminescence gradually reduced. However, the level of 80% of the maximum luminescence was still maintained after 90 minutes. Thus, the assay system employing the luciferase split assay of the present invention has enabled more prompt detection compared to the conventional protein-protein interaction detection system.

The luciferase split assay of the present invention can be applied to the GPCR other than SSTR2, namely ADRB2 (adrenergic beta 2 receptor, surface) (NM_000024), AGTRL1 (apelin receptor) (NM_00516), EDNRB (endothelin receptor type B) (NM_000115), and CCKBR (cholecystokinin B receptor) (NM_17685), and the results shown in FIG. 9 were obtained in similar experimental systems.

INDUSTRIAL APPLICABILITY

The present invention has enabled to provide a split luciferase assay system having a remarkably high detection sensitivity.

What is claimed is:

1. A fusion protein consisting of the amino acid sequence of SEQ ID NO: 1 and a peptide not derived from *Pyrearinus termitilluminans* luciferase.

2. A fusion protein consisting of an amino acid sequence selected from the group consisting of SEQ ID NOS: 2 to 6 fused with a peptide not derived from *Pyrearinus termitilluminans* luciferase.

3. A complex of a fusion protein of claim 1 and a fusion protein of claim 2.

4. The complex of claim 3 wherein said complex comprises
   a first fusion protein, said first fusion protein comprising a first protein fused to the amino acid of SEQ ID NO: 1; and
   a second fusion protein, said second fusion protein comprising a second protein fused to an amino acid sequence selected from the group consisting of SEQ ID NOs: 2 to 6, wherein said first and second proteins interact to form a complex.

5. The complex of claim 4 wherein said first and second proteins have mutual binding.

6. The complex of claim 4 wherein said complex further comprises a moiety that binds the first and second proteins.

7. The complex of claim 4 wherein either of said first protein and second protein is FK506-binding protein (FKBP) or is FKBP-binding domain (FRB).

8. The complex of claim 7 wherein the first protein is FKBP, and the second protein is FRB.

9. The complex of claim 6 wherein the moiety is rapamycin.

10. The complex of claim 4 wherein either of said first protein and second protein is a somatostatin receptor or is beta-arrestin.

11. The complex of claim 6 wherein the moiety is a G-protein coupled receptor.

12. The complex of claim 11 wherein the first protein is somatostatin type 2 receptor, the second protein is beta-arrestin, and the C terminus of the somatostain type 2 receptor is linked to SEQ ID NO: 1 and the N terminus of the beta-arrestin is linked to an amino acid sequence selected from the group consisting if SEQ ID NOs: 2 to 6.

13. A kit for detecting the binding of a first fusion protein and a second fusion protein in the presence of a moiety that binds to both the first and second fusion proteins, said kit comprising
   a first fusion protein, said first fusion protein comprising a first protein fused to the amino acid sequence of SEQ ID NO: 1; and
   a second fusion protein, said second fusion protein comprising a second protein fused to an amino acid sequence selected from the group consisting of SEQ ID NOs: 2 to 6, wherein said first and second proteins interact with said moiety to form a ternary complex.

* * * * *

SEQUENCE LISTING

```
<160> NUMBER OF SEQ ID NOS: 71

<210> SEQ ID NO 1
<211> LENGTH: 149
<212> TYPE: PRT
<213> ORGANISM: Pyrearinus termitilluminans

<400> SEQUENCE: 1

Thr Lys Gly Tyr Val Asn Asn Pro Gln Ala Thr Lys Glu Ala Ile Asp
1               5                   10                  15

Asp Asp Gly Trp Leu His Ser Gly Asp Phe Gly Tyr Tyr Asp Glu Asp
                20                  25                  30

Glu Tyr Phe Tyr Ile Val Asp Arg Tyr Lys Glu Leu Ile Lys Tyr Lys
            35                  40                  45

Gly Tyr Gln Val Ala Pro Val Glu Leu Glu Glu Ile Leu Leu Gln His
        50                  55                  60

Pro Gly Ile Arg Asp Val Ala Val Val Gly Ile Pro Asp Ile Glu Ala
65                  70                  75                  80

Gly Glu Leu Pro Ala Gly Phe Val Val Lys Gln Pro Gly Ala Gln Leu
                85                  90                  95

Thr Ala Lys Glu Val Tyr Asp Phe Leu Ala Gln Arg Val Ser His Ser
                100                 105                 110

Lys Tyr Leu Arg Gly Gly Val Arg Phe Val Asp Ser Ile Pro Arg Asn
            115                 120                 125

Val Thr Gly Lys Ile Ser Arg Lys Glu Leu Arg Glu Ala Leu Met Glu
        130                 135                 140

Lys Ala Ser Lys Leu
145

<210> SEQ ID NO 2
<211> LENGTH: 412
<212> TYPE: PRT
<213> ORGANISM: Pyrearinus termitilluminans
```

<400> SEQUENCE: 2

```
Met Glu Arg Glu Lys Asn Val Val Tyr Gly Pro Glu Pro Lys His Pro
1               5                   10                  15

Leu Gly Asn Phe Thr Ala Gly Glu Met Leu Tyr Asn Ala Leu His Lys
            20                  25                  30

His Ser His Ile Pro Gln Ala Ile Leu Asp Val Met Gly Asn Glu Ser
        35                  40                  45

Leu Ser Tyr Gln Glu Phe Phe Asp Thr Thr Val Lys Leu Gly Gln Ser
    50                  55                  60

Leu Gln Asn Cys Gly Tyr Lys Met Asn Asp Val Val Ser Ile Cys Ala
65                  70                  75                  80

Glu Asn Asn Lys Arg Phe Phe Ile Pro Ile Ile Ser Ala Trp Tyr Ile
                85                  90                  95

Gly Met Val Val Ala Pro Val Asn Glu Asp Tyr Ile Pro Asp Glu Leu
            100                 105                 110

Cys Lys Val Thr Gly Ile Ser Lys Pro Ile Leu Val Phe Thr Thr Arg
        115                 120                 125

Lys Ile Leu Pro Lys Val Leu Glu Val Lys Asp Arg Thr Asn Tyr Ile
    130                 135                 140

Lys Arg Ile Ile Ile Leu Asp Ser Glu Glu Asn Leu Leu Gly Cys Glu
145                 150                 155                 160

Ser Leu His Asn Phe Met Ser Arg Tyr Ser Asp Asn Asn Leu Gln Thr
                165                 170                 175

Phe Lys Pro Leu His Tyr Asp Pro Val Asp Gln Val Ala Ala Ile Leu
            180                 185                 190

Cys Ser Ser Gly Thr Thr Gly Leu Pro Lys Gly Val Met Gln Thr His
        195                 200                 205

Arg Asn Ile Cys Val Arg Leu Thr His Ala Ser Asp Pro Arg Val Gly
    210                 215                 220

Thr Gln Leu Ile Pro Gly Val Ser Val Leu Ala Tyr Leu Pro Phe Phe
225                 230                 235                 240

His Ala Phe Gly Phe Ser Ile Asn Leu Gly Tyr Phe Met Val Gly Leu
                245                 250                 255

Arg Val Val Met Leu Arg Arg Phe Asn Gln Glu Val Phe Leu Lys Ala
            260                 265                 270

Ile Gln Asp Tyr Glu Val Arg Ser Val Ile Asn Val Pro Ser Thr Ile
        275                 280                 285

Leu Phe Leu Ser Lys Ser Pro Leu Val Asp Lys Tyr Asp Leu Ser Thr
    290                 295                 300

Leu Ala Glu Leu Cys Cys Gly Ala Ala Pro Leu Ala Lys Glu Val Ala
305                 310                 315                 320

Glu Ile Ala Val Lys Arg Leu Asn Leu Pro Gly Ile Arg Cys Gly Tyr
                325                 330                 335

Gly Leu Thr Glu Ser Thr Ser Ala Asn Ile His Thr Leu His Asn Glu
            340                 345                 350

Phe Lys Ser Gly Ser Leu Gly Lys Val Thr Pro Tyr Met Ala Ala Lys
        355                 360                 365

Ile Ile Asp Arg Asn Thr Gly Glu Ala Leu Gly Pro Asn Gln Val Gly
    370                 375                 380

Glu Leu Cys Ile Trp Gly Pro Met Val Thr Lys Gly Tyr Val Asn Asn
385                 390                 395                 400

Pro Gln Ala Thr Lys Glu Ala Ile Asp Asp Gly
                405                 410
```

<210> SEQ ID NO 3
<211> LENGTH: 413
<212> TYPE: PRT
<213> ORGANISM: Pyrearinus termitilluminans

<400> SEQUENCE: 3

```
Met Glu Arg Glu Lys Asn Val Val Tyr Gly Pro Glu Pro Lys His Pro
1               5                   10                  15

Leu Gly Asn Phe Thr Ala Gly Glu Met Leu Tyr Asn Ala Leu His Lys
            20                  25                  30

His Ser His Ile Pro Gln Ala Ile Leu Asp Val Met Gly Asn Glu Ser
        35                  40                  45

Leu Ser Tyr Gln Glu Phe Phe Asp Thr Thr Val Lys Leu Gly Gln Ser
    50                  55                  60

Leu Gln Asn Cys Gly Tyr Lys Met Asn Asp Val Val Ser Ile Cys Ala
65                  70                  75                  80

Glu Asn Asn Lys Arg Phe Phe Ile Pro Ile Ile Ser Ala Trp Tyr Ile
                85                  90                  95

Gly Met Val Val Ala Pro Val Asn Glu Asp Tyr Ile Pro Asp Glu Leu
            100                 105                 110

Cys Lys Val Thr Gly Ile Ser Lys Pro Ile Leu Val Phe Thr Thr Arg
        115                 120                 125

Lys Ile Leu Pro Lys Val Leu Glu Val Lys Asp Arg Thr Asn Tyr Ile
    130                 135                 140

Lys Arg Ile Ile Ile Leu Asp Ser Glu Glu Asn Leu Leu Gly Cys Glu
145                 150                 155                 160

Ser Leu His Asn Phe Met Ser Arg Tyr Ser Asp Asn Asn Leu Gln Thr
                165                 170                 175

Phe Lys Pro Leu His Tyr Asp Pro Val Asp Gln Val Ala Ala Ile Leu
            180                 185                 190

Cys Ser Ser Gly Thr Thr Gly Leu Pro Lys Gly Val Met Gln Thr His
        195                 200                 205

Arg Asn Ile Cys Val Arg Leu Thr His Ala Ser Asp Pro Arg Val Gly
    210                 215                 220

Thr Gln Leu Ile Pro Gly Val Ser Val Leu Ala Tyr Leu Pro Phe Phe
225                 230                 235                 240

His Ala Phe Gly Phe Ser Ile Asn Leu Gly Tyr Phe Met Val Gly Leu
                245                 250                 255

Arg Val Val Met Leu Arg Arg Phe Asn Gln Glu Val Phe Leu Lys Ala
            260                 265                 270

Ile Gln Asp Tyr Glu Val Arg Ser Val Ile Asn Val Pro Ser Thr Ile
    275                 280                 285

Leu Phe Leu Ser Lys Ser Pro Leu Val Asp Lys Tyr Asp Leu Ser Thr
290                 295                 300

Leu Ala Glu Leu Cys Cys Gly Ala Ala Pro Leu Ala Lys Glu Val Ala
305                 310                 315                 320

Glu Ile Ala Val Lys Arg Leu Asn Leu Pro Gly Ile Arg Cys Gly Tyr
                325                 330                 335

Gly Leu Thr Glu Ser Thr Ser Ala Asn Ile His Thr Leu His Asn Glu
            340                 345                 350

Phe Lys Ser Gly Ser Leu Gly Lys Val Thr Pro Tyr Met Ala Ala Lys
        355                 360                 365

Ile Ile Asp Arg Asn Thr Gly Glu Ala Leu Gly Pro Asn Gln Val Gly
    370                 375                 380
```

```
Glu Leu Cys Ile Trp Gly Pro Met Val Thr Lys Gly Tyr Val Asn Asn
385                 390                 395                 400

Pro Gln Ala Thr Lys Glu Ala Ile Asp Asp Gly Trp
                405                 410
```

<210> SEQ ID NO 4
<211> LENGTH: 414
<212> TYPE: PRT
<213> ORGANISM: Pyrearinus termitilluminans

<400> SEQUENCE: 4

```
Met Glu Arg Glu Lys Asn Val Val Tyr Gly Pro Glu Pro Lys His Pro
1               5                   10                  15

Leu Gly Asn Phe Thr Ala Gly Glu Met Leu Tyr Asn Ala Leu His Lys
                20                  25                  30

His Ser His Ile Pro Gln Ala Ile Leu Asp Val Met Gly Asn Glu Ser
            35                  40                  45

Leu Ser Tyr Gln Glu Phe Phe Asp Thr Val Lys Leu Gly Gln Ser
    50                  55                  60

Leu Gln Asn Cys Gly Tyr Lys Met Asn Asp Val Val Ser Ile Cys Ala
65                  70                  75                  80

Glu Asn Asn Lys Arg Phe Phe Ile Pro Ile Ile Ser Ala Trp Tyr Ile
                85                  90                  95

Gly Met Val Val Ala Pro Val Asn Glu Asp Tyr Ile Pro Asp Glu Leu
                100                 105                 110

Cys Lys Val Thr Gly Ile Ser Lys Pro Ile Leu Val Phe Thr Thr Arg
            115                 120                 125

Lys Ile Leu Pro Lys Val Leu Glu Val Lys Asp Arg Thr Asn Tyr Ile
130                 135                 140

Lys Arg Ile Ile Ile Leu Asp Ser Glu Glu Asn Leu Leu Gly Cys Glu
145                 150                 155                 160

Ser Leu His Asn Phe Met Ser Arg Tyr Ser Asp Asn Asn Leu Gln Thr
                165                 170                 175

Phe Lys Pro Leu His Tyr Asp Pro Val Asp Gln Val Ala Ala Ile Leu
            180                 185                 190

Cys Ser Ser Gly Thr Thr Gly Leu Pro Lys Gly Val Met Gln Thr His
    195                 200                 205

Arg Asn Ile Cys Val Arg Leu Thr His Ala Ser Asp Pro Arg Val Gly
210                 215                 220

Thr Gln Leu Ile Pro Gly Val Ser Val Leu Ala Tyr Leu Pro Phe Phe
225                 230                 235                 240

His Ala Phe Gly Phe Ser Ile Asn Leu Gly Tyr Phe Met Val Gly Leu
                245                 250                 255

Arg Val Val Met Leu Arg Arg Phe Asn Gln Glu Val Phe Leu Lys Ala
                260                 265                 270

Ile Gln Asp Tyr Glu Val Arg Ser Val Ile Asn Val Pro Ser Thr Ile
    275                 280                 285

Leu Phe Leu Ser Lys Ser Pro Leu Val Asp Lys Tyr Asp Leu Ser Thr
290                 295                 300

Leu Ala Glu Leu Cys Cys Gly Ala Ala Pro Leu Ala Lys Glu Val Ala
305                 310                 315                 320

Glu Ile Ala Val Lys Arg Leu Asn Leu Pro Gly Ile Arg Cys Gly Tyr
                325                 330                 335

Gly Leu Thr Glu Ser Thr Ser Ala Asn Ile His Thr Leu His Asn Glu
            340                 345                 350
```

-continued

```
Phe Lys Ser Gly Ser Leu Gly Lys Val Thr Pro Tyr Met Ala Ala Lys
            355                 360                 365

Ile Ile Asp Arg Asn Thr Gly Glu Ala Leu Gly Pro Asn Gln Val Gly
370                 375                 380

Glu Leu Cys Ile Trp Gly Pro Met Val Thr Lys Gly Tyr Val Asn Asn
385                 390                 395                 400

Pro Gln Ala Thr Lys Glu Ala Ile Asp Asp Gly Trp Leu
                405                 410

<210> SEQ ID NO 5
<211> LENGTH: 415
<212> TYPE: PRT
<213> ORGANISM: Pyrearinus termitilluminans

<400> SEQUENCE: 5

Met Glu Arg Glu Lys Asn Val Val Tyr Gly Pro Glu Pro Lys His Pro
1               5                   10                  15

Leu Gly Asn Phe Thr Ala Gly Glu Met Leu Tyr Asn Ala Leu His Lys
            20                  25                  30

His Ser His Ile Pro Gln Ala Ile Leu Asp Val Met Gly Asn Glu Ser
        35                  40                  45

Leu Ser Tyr Gln Glu Phe Phe Asp Thr Thr Val Lys Leu Gly Gln Ser
50                  55                  60

Leu Gln Asn Cys Gly Tyr Lys Met Asn Asp Val Val Ser Ile Cys Ala
65                  70                  75                  80

Glu Asn Asn Lys Arg Phe Phe Ile Pro Ile Ile Ser Ala Trp Tyr Ile
                85                  90                  95

Gly Met Val Val Ala Pro Val Asn Glu Asp Tyr Ile Pro Asp Glu Leu
            100                 105                 110

Cys Lys Val Thr Gly Ile Ser Lys Pro Ile Leu Val Phe Thr Thr Arg
        115                 120                 125

Lys Ile Leu Pro Lys Val Leu Glu Val Lys Asp Arg Thr Asn Tyr Ile
    130                 135                 140

Lys Arg Ile Ile Ile Leu Asp Ser Glu Glu Asn Leu Leu Gly Cys Glu
145                 150                 155                 160

Ser Leu His Asn Phe Met Ser Arg Tyr Ser Asp Asn Asn Leu Gln Thr
                165                 170                 175

Phe Lys Pro Leu His Tyr Asp Pro Val Asp Gln Val Ala Ala Ile Leu
            180                 185                 190

Cys Ser Ser Gly Thr Thr Gly Leu Pro Lys Gly Val Met Gln Thr His
        195                 200                 205

Arg Asn Ile Cys Val Arg Leu Thr His Ala Ser Asp Pro Arg Val Gly
    210                 215                 220

Thr Gln Leu Ile Pro Gly Val Ser Val Leu Ala Tyr Leu Pro Phe Phe
225                 230                 235                 240

His Ala Phe Gly Phe Ser Ile Asn Leu Gly Tyr Phe Met Val Gly Leu
                245                 250                 255

Arg Val Val Met Leu Arg Arg Phe Asn Gln Glu Val Phe Leu Lys Ala
            260                 265                 270

Ile Gln Asp Tyr Glu Val Arg Ser Val Ile Asn Val Pro Ser Thr Ile
        275                 280                 285

Leu Phe Leu Ser Lys Ser Pro Leu Val Asp Lys Tyr Asp Leu Ser Thr
    290                 295                 300

Leu Ala Glu Leu Cys Cys Gly Ala Ala Pro Leu Ala Lys Glu Val Ala
305                 310                 315                 320
```

Glu Ile Ala Val Lys Arg Leu Asn Leu Pro Gly Ile Arg Cys Gly Tyr
            325                 330                 335

Gly Leu Thr Glu Ser Thr Ser Ala Asn Ile His Thr Leu His Asn Glu
            340                 345                 350

Phe Lys Ser Gly Ser Leu Gly Lys Val Thr Pro Tyr Met Ala Ala Lys
            355                 360                 365

Ile Ile Asp Arg Asn Thr Gly Glu Ala Leu Gly Pro Asn Gln Val Gly
            370                 375                 380

Glu Leu Cys Ile Trp Gly Pro Met Val Thr Lys Gly Tyr Val Asn Asn
385                 390                 395                 400

Pro Gln Ala Thr Lys Glu Ala Ile Asp Asp Gly Trp Leu His
            405                 410                 415

<210> SEQ ID NO 6
<211> LENGTH: 416
<212> TYPE: PRT
<213> ORGANISM: Pyrearinus termitilluminans

<400> SEQUENCE: 6

Met Glu Arg Glu Lys Asn Val Val Tyr Gly Pro Glu Pro Lys His Pro
1               5                   10                  15

Leu Gly Asn Phe Thr Ala Gly Glu Met Leu Tyr Asn Ala Leu His Lys
            20                  25                  30

His Ser His Ile Pro Gln Ala Ile Leu Asp Val Met Gly Asn Glu Ser
            35                  40                  45

Leu Ser Tyr Gln Glu Phe Phe Asp Thr Thr Val Lys Leu Gly Gln Ser
        50                  55                  60

Leu Gln Asn Cys Gly Tyr Lys Met Asn Asp Val Val Ser Ile Cys Ala
65                  70                  75                  80

Glu Asn Asn Lys Arg Phe Phe Ile Pro Ile Ile Ser Ala Trp Tyr Ile
            85                  90                  95

Gly Met Val Val Ala Pro Val Asn Glu Asp Tyr Ile Pro Asp Glu Leu
            100                 105                 110

Cys Lys Val Thr Gly Ile Ser Lys Pro Ile Leu Val Phe Thr Thr Arg
            115                 120                 125

Lys Ile Leu Pro Lys Val Leu Glu Val Lys Asp Arg Thr Asn Tyr Ile
        130                 135                 140

Lys Arg Ile Ile Ile Leu Asp Ser Glu Glu Asn Leu Leu Gly Cys Glu
145                 150                 155                 160

Ser Leu His Asn Phe Met Ser Arg Tyr Ser Asp Asn Asn Leu Gln Thr
            165                 170                 175

Phe Lys Pro Leu His Tyr Asp Pro Val Asp Gln Val Ala Ala Ile Leu
            180                 185                 190

Cys Ser Ser Gly Thr Thr Gly Leu Pro Lys Gly Val Met Gln Thr His
            195                 200                 205

Arg Asn Ile Cys Val Arg Leu Thr His Ala Ser Asp Pro Arg Val Gly
        210                 215                 220

Thr Gln Leu Ile Pro Gly Val Ser Val Leu Ala Tyr Leu Pro Phe Phe
225                 230                 235                 240

His Ala Phe Gly Phe Ser Ile Asn Leu Gly Tyr Phe Met Val Gly Leu
            245                 250                 255

Arg Val Val Met Leu Arg Arg Phe Asn Gln Glu Val Phe Leu Lys Ala
            260                 265                 270

Ile Gln Asp Tyr Glu Val Arg Ser Val Ile Asn Val Pro Ser Thr Ile
            275                 280                 285

```
Leu Phe Leu Ser Lys Ser Pro Leu Val Asp Lys Tyr Asp Leu Ser Thr
            290                 295                 300

Leu Ala Glu Leu Cys Cys Gly Ala Ala Pro Leu Ala Lys Glu Val Ala
305                 310                 315                 320

Glu Ile Ala Val Lys Arg Leu Asn Leu Pro Gly Ile Arg Cys Gly Tyr
                325                 330                 335

Gly Leu Thr Glu Ser Thr Ser Ala Asn Ile His Thr Leu His Asn Glu
            340                 345                 350

Phe Lys Ser Gly Ser Leu Gly Lys Val Thr Pro Tyr Met Ala Ala Lys
                355                 360                 365

Ile Ile Asp Arg Asn Thr Gly Glu Ala Leu Gly Pro Asn Gln Val Gly
            370                 375                 380

Glu Leu Cys Ile Trp Gly Pro Met Val Thr Lys Gly Tyr Val Asn Asn
385                 390                 395                 400

Pro Gln Ala Thr Lys Glu Ala Ile Asp Asp Asp Gly Trp Leu His Ser
                405                 410                 415

<210> SEQ ID NO 7
<211> LENGTH: 1611
<212> TYPE: DNA
<213> ORGANISM: Artificial Sequence
<220> FEATURE:
<223> OTHER INFORMATION: myc-His

<400> SEQUENCE: 7
aagcttaccg ccatggagag agagaagaac gtggtgtacg gccccgagcc caagcaccct      60
ctgggcaact tcaccgccgg cgagatgctg tacaacgctc tgcacaagca ctcccacatc     120
ccccaggcca tcctggacgt gatgggcaac gagtcccttt cctaccagga gttcttcgac     180
actactgtga agctgggcca gagcctccag aactgtggct acaagatgaa cgatgtcgtg     240
tcgatctgtg cagagaacaa caagagattc ttcatcccca tcatctccgc ctggtacatc     300
ggcatggtgg tggcccctgt gaacgaggac tatatcccag acgagctgtg taaagtgacc     360
ggcatctcca gccgatcct ggtcttcacc actaggaaga tcctgcctaa ggttttggag     420
gttaaagaca gaaccaacta cataaagagg atcatcatac tggactctga agagaacctg     480
ctgggctgcg agagcctgca aacttcatg tccaggtact ccgacaacaa cctccaaaca     540
ttcaagcctc tgcactacga ccctgtggac caggtagccg ccatcctgtg ctcctccggc     600
acaaccggcc tgcctaaagg cgtgatgcag acccacagga acatctgtgt gagactcaca     660
cacgcatctg accccagagt gggtacacaa ctcatcccccg cgtatccgt gctggcctac     720 ctgccattct ccacgccttc cggcttcagt atcaacctgg ctatttcat ggtgggcctg     780 agagtggtga tgctccgaag gtttaaccag gaggtgttcc tgaaggccat ccaggactac     840
gaggtgagga gcgtgatcaa cgttccctcc acaatcctgt tcctgtccaa gagccctctg     900
gtggacaagt acgacctatc caccctggcg gagctgtgct gtggagccgc tcctctggcg     960
aaggaggtgg ccgagatcgc cgtgaagagg ctgaacctgc agggatacg tgtggctac    1020 ggtctaacag agtctacctc cgccaacatc catactctgc acaacgagtt caagtccggc    1080
tccctgggca aggtgacacc ttacatggcc gccaagatca tcgacaggaa caccggcgag    1140
gccctgggtc caaaccaggt gggcgagctg tgcatctggg gacctatggt aacaaaaggc    1200
tatgtgaaca acccacaggc tactaaggag gccatcgacg acgacggctg gctgcacgga    1260
ggaggcggag gatccatggg cgtgcaggtg gagactatct ccccaggaga cgggcgcacc    1320
ttccccaagc gcggccagac ctgcgtggtg cactacaccg gatgcttga agatggaaag    1380
```

```
aaatttgatt cctcccggga cagaaacaag cccttttaagt ttatgctagg caagcaggag    1440
gtgatccgag gctgggaaga aggggttgcc cagatgagtg tgggtcagag agccaaactg    1500
actatatctc cagattatgc ctatggtgcc actgggcacc caggcatcat cccaccacat    1560
gccactctcg tcttcgatgt ggagcttcta aaactggaac gctcgagtct a             1611
```

<210> SEQ ID NO 8
<211> LENGTH: 790
<212> TYPE: DNA
<213> ORGANISM: Artificial Sequence
<220> FEATURE:
<223> OTHER INFORMATION: V5-His

<400> SEQUENCE: 8

```
ggatccccg ggctgcagga attctatggt agccatcctc tggcatgaga tgtggcatga      60
aggtctagaa gaggcctctc gcttgtactt tggggagagg aacgtcaaag gcatgtttga    120
ggtgctggag cccctgcatg ctatgatgga acgcggtccc cagaccctga aggaaacgtc    180
ctttaatcag gcatatggtc gagatttaat ggaggcacaa gaatggtgcc gaaagtacat    240
gaaatcaggg aacgtcaagg acctcaccca agcctgggac ctctactatc acgtgttcag    300
acggatatca cgctcgagtg gaggcggcgg aacaaaaggc tatgtgaaca acccacaggc    360
tactaaggag gccatcgacg acgacggctg gctgcactct ggcgacttcg gctactacga    420
cgaggacgag tatttctaca tcgtggaccg gtacaaggag ctgatcaaat acaagggcta    480
tcaggtcgcc cctgtggagc tggaggagat cctccttcag cacccaggca tcagggacgt    540
ggccgtcgtg ggtatccctg acatcgaggc cggcgagctg ccagccggct tcgtggtgaa    600
gcagcccggc gcccaactca ccgctaagga ggtgtacgac ttcctggccc agagggtgtc    660
tcactccaag tacctgaggg gcggcgtaag gttcgtggac tctatcccca ggaacgtgac    720
aggcaagatt agtcgaaaag agctgaggga ggccctgatg gagaaggctt ctaagctggg    780
cccgcggttc                                                           790
```

<210> SEQ ID NO 9
<211> LENGTH: 33
<212> TYPE: DNA
<213> ORGANISM: Artificial Sequence
<220> FEATURE:
<223> OTHER INFORMATION: PCR primer

<400> SEQUENCE: 9

```
aagcttgcca tggtaaagcg tgagaaaaat gtc                                   33
```

<210> SEQ ID NO 10
<211> LENGTH: 36
<212> TYPE: DNA
<213> ORGANISM: Artificial Sequence
<220> FEATURE:
<223> OTHER INFORMATION: PCR primer

<400> SEQUENCE: 10

```
ggatcctccg cctcctccgc cgtcgtcgat ggcctc                                36
```

<210> SEQ ID NO 11
<211> LENGTH: 46
<212> TYPE: DNA
<213> ORGANISM: Artificial Sequence
<220> FEATURE:
<223> OTHER INFORMATION: PCR primer

<400> SEQUENCE: 11

-continued aggctcgagt ggaggcggcg gaggctggct gcactctggc gacttc     46

<210> SEQ ID NO 12
<211> LENGTH: 35
<212> TYPE: DNA
<213> ORGANISM: Artificial Sequence
<220> FEATURE:
<223> OTHER INFORMATION: PCR primer

<400> SEQUENCE: 12
cgcgggccca gcttagaagc cttctccatc agggc     35

<210> SEQ ID NO 13
<211> LENGTH: 33
<212> TYPE: DNA
<213> ORGANISM: Artificial Sequence
<220> FEATURE:
<223> OTHER INFORMATION: PCR primer

<400> SEQUENCE: 13
tttaagctta ccgccatgga gagagagaag aac     33

<210> SEQ ID NO 14
<211> LENGTH: 39
<212> TYPE: DNA
<213> ORGANISM: Artificial Sequence
<220> FEATURE:
<223> OTHER INFORMATION: PCR primer

<400> SEQUENCE: 14
tttggatcct ccgcctcctc cagtagcctg tgggttgtt     39

<210> SEQ ID NO 15
<211> LENGTH: 39
<212> TYPE: DNA
<213> ORGANISM: Artificial Sequence
<220> FEATURE:
<223> OTHER INFORMATION: PCR primer

<400> SEQUENCE: 15
tttggatcct ccgcctcctc ccttagtagc ctgtgggtt     39

<210> SEQ ID NO 16
<211> LENGTH: 39
<212> TYPE: DNA
<213> ORGANISM: Artificial Sequence
<220> FEATURE:
<223> OTHER INFORMATION: PCR primer

<400> SEQUENCE: 16
tttggatcct ccgcctcctc cctccttagt agcctgtgg     39

<210> SEQ ID NO 17
<211> LENGTH: 39
<212> TYPE: DNA
<213> ORGANISM: Artificial Sequence
<220> FEATURE:
<223> OTHER INFORMATION: PCR primer

<400> SEQUENCE: 17
tttggatcct ccgcctcctc cggcctcctt agtagcctg     39

<210> SEQ ID NO 18
<211> LENGTH: 39
<212> TYPE: DNA
<213> ORGANISM: Artificial Sequence
<220> FEATURE:

-continued

<223> OTHER INFORMATION: PCR primer

<400> SEQUENCE: 18
tttggatcct ccgcctcctc cgatggcctc cttagtagc           39

<210> SEQ ID NO 19
<211> LENGTH: 39
<212> TYPE: DNA
<213> ORGANISM: Artificial Sequence
<220> FEATURE:
<223> OTHER INFORMATION: PCR primer

<400> SEQUENCE: 19
tttggatcct ccgcctcctc cgtcgatggc ctccttagt           39

<210> SEQ ID NO 20
<211> LENGTH: 39
<212> TYPE: DNA
<213> ORGANISM: Artificial Sequence
<220> FEATURE:
<223> OTHER INFORMATION: PCR primer

<400> SEQUENCE: 20
tttggatcct ccgcctcctc cgtcgtcgat ggcctcctt           39

<210> SEQ ID NO 21
<211> LENGTH: 39
<212> TYPE: DNA
<213> ORGANISM: Artificial Sequence
<220> FEATURE:
<223> OTHER INFORMATION: PCR primer

<400> SEQUENCE: 21
tttggatcct ccgcctcctc cgtcgtcgtc gatggcctc           39

<210> SEQ ID NO 22
<211> LENGTH: 39
<212> TYPE: DNA
<213> ORGANISM: Artificial Sequence
<220> FEATURE:
<223> OTHER INFORMATION: PCR primer

<400> SEQUENCE: 22
tttggatcct ccgcctcctc cgccgtcgtc gtcgatggc           39

<210> SEQ ID NO 23
<211> LENGTH: 39
<212> TYPE: DNA
<213> ORGANISM: Artificial Sequence
<220> FEATURE:
<223> OTHER INFORMATION: PCR primer

<400> SEQUENCE: 23
tttggatcct ccgcctcctc cccagccgtc gtcgtcgat           39

<210> SEQ ID NO 24
<211> LENGTH: 40
<212> TYPE: DNA
<213> ORGANISM: Artificial Sequence
<220> FEATURE:
<223> OTHER INFORMATION: PCR primer

<400> SEQUENCE: 24
aggctcgagt ggaggcggcg gaacaaaagg ctatgtgaac          40

<210> SEQ ID NO 25

```
<210> SEQ ID NO 25
<211> LENGTH: 31
<212> TYPE: DNA
<213> ORGANISM: Artificial Sequence
<220> FEATURE:
<223> OTHER INFORMATION: PCR primer

<400> SEQUENCE: 25
ttttccgcgg gcccagctta gaagccttct c                           31

<210> SEQ ID NO 26
<211> LENGTH: 39
<212> TYPE: DNA
<213> ORGANISM: Artificial Sequence
<220> FEATURE:
<223> OTHER INFORMATION: PCR primer

<400> SEQUENCE: 26
tttggatcct ccgcctcctc ccagccagcc gtcgtcgtc                   39

<210> SEQ ID NO 27
<211> LENGTH: 39
<212> TYPE: DNA
<213> ORGANISM: Artificial Sequence
<220> FEATURE:
<223> OTHER INFORMATION: PCR primer

<400> SEQUENCE: 27
tttggatcct ccgcctcctc cgtgcagcca gccgtcgtc                   39

<210> SEQ ID NO 28
<211> LENGTH: 39
<212> TYPE: DNA
<213> ORGANISM: Artificial Sequence
<220> FEATURE:
<223> OTHER INFORMATION: PCR primer

<400> SEQUENCE: 28
tttggatcct ccgcctcctc cagagtgcag ccagccgtc                   39

<210> SEQ ID NO 29
<211> LENGTH: 39
<212> TYPE: DNA
<213> ORGANISM: Artificial Sequence
<220> FEATURE:
<223> OTHER INFORMATION: PCR primer

<400> SEQUENCE: 29
tttggatcct ccgcctcctc cgccagagtg cagccagcc                   39

<210> SEQ ID NO 30
<211> LENGTH: 40
<212> TYPE: DNA
<213> ORGANISM: Artificial Sequence
<220> FEATURE:
<223> OTHER INFORMATION: PCR primer

<400> SEQUENCE: 30
aggctcgagt ggaggcggcg gaaaaggcta tgtgaacaac                  40

<210> SEQ ID NO 31
<211> LENGTH: 40
<212> TYPE: DNA
<213> ORGANISM: Artificial Sequence
<220> FEATURE:
<223> OTHER INFORMATION: PCR primer

<400> SEQUENCE: 31
```

-continued aggctcgagt ggaggcggcg gaggctatgt gaacaaccca        40

<210> SEQ ID NO 32
<211> LENGTH: 40
<212> TYPE: DNA
<213> ORGANISM: Artificial Sequence
<220> FEATURE:
<223> OTHER INFORMATION: PCR primer

<400> SEQUENCE: 32
aggctcgagt ggaggcggcg gatatgtgaa caacccacag        40

<210> SEQ ID NO 33
<211> LENGTH: 40
<212> TYPE: DNA
<213> ORGANISM: Artificial Sequence
<220> FEATURE:
<223> OTHER INFORMATION: PCR primer

<400> SEQUENCE: 33
aggctcgagt ggaggcggcg gagtgaacaa cccacaggct        40

<210> SEQ ID NO 34
<211> LENGTH: 40
<212> TYPE: DNA
<213> ORGANISM: Artificial Sequence
<220> FEATURE:
<223> OTHER INFORMATION: PCR primer

<400> SEQUENCE: 34
aggctcgagt ggaggcggcg gaaacaaccc acaggctact        40

<210> SEQ ID NO 35
<211> LENGTH: 40
<212> TYPE: DNA
<213> ORGANISM: Artificial Sequence
<220> FEATURE:
<223> OTHER INFORMATION: PCR primer

<400> SEQUENCE: 35
aggctcgagt ggaggcggcg gaccacaggc tactaaggag        40

<210> SEQ ID NO 36
<211> LENGTH: 40
<212> TYPE: DNA
<213> ORGANISM: Artificial Sequence
<220> FEATURE:
<223> OTHER INFORMATION: PCR primer

<400> SEQUENCE: 36
aggctcgagt ggaggcggcg gacaggctac taaggaggcc        40

<210> SEQ ID NO 37
<211> LENGTH: 40
<212> TYPE: DNA
<213> ORGANISM: Artificial Sequence
<220> FEATURE:
<223> OTHER INFORMATION: PCR primer

<400> SEQUENCE: 37
aggctcgagt ggaggcggcg gaactaagga ggccatcgac        40

<210> SEQ ID NO 38
<211> LENGTH: 40
<212> TYPE: DNA
<213> ORGANISM: Artificial Sequence
<220> FEATURE:

<223> OTHER INFORMATION: PCR primer

<400> SEQUENCE: 38
aggctcgagt ggaggcggcg gaaaggaggc catcgacgac          40

<210> SEQ ID NO 39
<211> LENGTH: 40
<212> TYPE: DNA
<213> ORGANISM: Artificial Sequence
<220> FEATURE:
<223> OTHER INFORMATION: PCR primer

<400> SEQUENCE: 39
aggctcgagt ggaggcggcg gagaggccat cgacgacgac          40

<210> SEQ ID NO 40
<211> LENGTH: 40
<212> TYPE: DNA
<213> ORGANISM: Artificial Sequence
<220> FEATURE:
<223> OTHER INFORMATION: PCR primer

<400> SEQUENCE: 40
aggctcgagt ggaggcggcg gagccatcga cgacgacggc          40

<210> SEQ ID NO 41
<211> LENGTH: 40
<212> TYPE: DNA
<213> ORGANISM: Artificial Sequence
<220> FEATURE:
<223> OTHER INFORMATION: PCR primer

<400> SEQUENCE: 41
aggctcgagt ggaggcggcg gaatcgacga cgacggctgg          40

<210> SEQ ID NO 42
<211> LENGTH: 40
<212> TYPE: DNA
<213> ORGANISM: Artificial Sequence
<220> FEATURE:
<223> OTHER INFORMATION: PCR primer

<400> SEQUENCE: 42
aggctcgagt ggaggcggcg gagacgacga cggctggctg          40

<210> SEQ ID NO 43
<211> LENGTH: 40
<212> TYPE: DNA
<213> ORGANISM: Artificial Sequence
<220> FEATURE:
<223> OTHER INFORMATION: PCR primer

<400> SEQUENCE: 43
aggctcgagt ggaggcggcg gagacgacgg ctggctgcac          40

<210> SEQ ID NO 44
<211> LENGTH: 40
<212> TYPE: DNA
<213> ORGANISM: Artificial Sequence
<220> FEATURE:
<223> OTHER INFORMATION: PCR primer

<400> SEQUENCE: 44
aggctcgagt ggaggcggcg gagacggctg gctgcactct          40

<210> SEQ ID NO 45

```
<211> LENGTH: 40
<212> TYPE: DNA
<213> ORGANISM: Artificial Sequence
<220> FEATURE:
<223> OTHER INFORMATION: PCR primer

<400> SEQUENCE: 45
aggctcgagt ggaggcggcg gaggctggct gcactctggc                    40

<210> SEQ ID NO 46
<211> LENGTH: 40
<212> TYPE: DNA
<213> ORGANISM: Artificial Sequence
<220> FEATURE:
<223> OTHER INFORMATION: PCR primer

<400> SEQUENCE: 46
aggctcgagt ggaggcggcg gatggctgca ctctggcgac                    40

<210> SEQ ID NO 47
<211> LENGTH: 43
<212> TYPE: DNA
<213> ORGANISM: Artificial Sequence
<220> FEATURE:
<223> OTHER INFORMATION: PCR primer

<400> SEQUENCE: 47
aggctcgagt ggaggcggcg gaaacccaca ggctactaag gag                43

<210> SEQ ID NO 48
<211> LENGTH: 43
<212> TYPE: DNA
<213> ORGANISM: Artificial Sequence
<220> FEATURE:
<223> OTHER INFORMATION: PCR primer

<400> SEQUENCE: 48
aggctcgagt ggaggcggcg gagctactaa ggaggccatc gac                43

<210> SEQ ID NO 49
<211> LENGTH: 40
<212> TYPE: DNA
<213> ORGANISM: Artificial Sequence
<220> FEATURE:
<223> OTHER INFORMATION: PCR primer

<400> SEQUENCE: 49
aggctcgagt ggaggcggcg gagtaacaaa aggctatgtg                    40

<210> SEQ ID NO 50
<211> LENGTH: 40
<212> TYPE: DNA
<213> ORGANISM: Artificial Sequence
<220> FEATURE:
<223> OTHER INFORMATION: PCR primer

<400> SEQUENCE: 50
aggctcgagt ggaggcggcg gaatggtaac aaaaggctat                    40

<210> SEQ ID NO 51
<211> LENGTH: 40
<212> TYPE: DNA
<213> ORGANISM: Artificial Sequence
<220> FEATURE:
<223> OTHER INFORMATION: PCR primer

<400> SEQUENCE: 51
```

```
aggctcgagt ggaggcggcg gacctatggt aacaaaaggc                    40
```

<210> SEQ ID NO 52
<211> LENGTH: 40
<212> TYPE: DNA
<213> ORGANISM: Artificial Sequence
<220> FEATURE:
<223> OTHER INFORMATION: PCR primer

<400> SEQUENCE: 52

```
aggctcgagt ggaggcggcg gaggacctat ggtaacaaaa                    40
```

<210> SEQ ID NO 53
<211> LENGTH: 40
<212> TYPE: DNA
<213> ORGANISM: Artificial Sequence
<220> FEATURE:
<223> OTHER INFORMATION: PCR primer

<400> SEQUENCE: 53

```
aggctcgagt ggaggcggcg gatggggacc tatggtaaca                    40
```

<210> SEQ ID NO 54
<211> LENGTH: 37
<212> TYPE: DNA
<213> ORGANISM: Artificial Sequence
<220> FEATURE:
<223> OTHER INFORMATION: PCR primer

<400> SEQUENCE: 54

```
aaaggatcca tgggggagaa acccgggacc agggtct                       37
```

<210> SEQ ID NO 55
<211> LENGTH: 30
<212> TYPE: DNA
<213> ORGANISM: Artificial Sequence
<220> FEATURE:
<223> OTHER INFORMATION: PCR primer

<400> SEQUENCE: 55

```
aagaattcca gcagagttga tcatcatagt                               30
```

<210> SEQ ID NO 56
<211> LENGTH: 30
<212> TYPE: DNA
<213> ORGANISM: Artificial Sequence
<220> FEATURE:
<223> OTHER INFORMATION: PCR primer

<400> SEQUENCE: 56

```
ttggatccat ggacatggcg gatgagccac                               30
```

<210> SEQ ID NO 57
<211> LENGTH: 36
<212> TYPE: DNA
<213> ORGANISM: Artificial Sequence
<220> FEATURE:
<223> OTHER INFORMATION: PCR primer

<400> SEQUENCE: 57

```
tttctcgagc cgatactggt ttggaggtct ccattg                        36
```

<210> SEQ ID NO 58
<211> LENGTH: 42
<212> TYPE: DNA
<213> ORGANISM: Artificial Sequence
<220> FEATURE:

<223> OTHER INFORMATION: PCR primer

<400> SEQUENCE: 58
aggctcgagt ggcggtggag gtagtggagg cggcggaaca aa        42

<210> SEQ ID NO 59
<211> LENGTH: 42
<212> TYPE: DNA
<213> ORGANISM: Artificial Sequence
<220> FEATURE:
<223> OTHER INFORMATION: PCR primer

<400> SEQUENCE: 59
aggctcgagt ggtggtgggg gcagtggcgg tggaggtagt gg        42

<210> SEQ ID NO 60
<211> LENGTH: 46
<212> TYPE: DNA
<213> ORGANISM: Artificial Sequence
<220> FEATURE:
<223> OTHER INFORMATION: PCR primer

<400> SEQUENCE: 60
aggctcgagt ggaggtggcg gttctggtgg tgggggcagt ggcggt        46

<210> SEQ ID NO 61
<211> LENGTH: 27
<212> TYPE: DNA
<213> ORGANISM: Artificial Sequence
<220> FEATURE:
<223> OTHER INFORMATION: PCR primer

<400> SEQUENCE: 61
tttccgcggc agcttagaag ccttctc        27

<210> SEQ ID NO 62
<211> LENGTH: 29
<212> TYPE: DNA
<213> ORGANISM: Artificial Sequence
<220> FEATURE:
<223> OTHER INFORMATION: PCR primer

<400> SEQUENCE: 62
tttaagctta tgcagccgcc tccaagtct        29

<210> SEQ ID NO 63
<211> LENGTH: 38
<212> TYPE: DNA
<213> ORGANISM: Artificial Sequence
<220> FEATURE:
<223> OTHER INFORMATION: PCR primer

<400> SEQUENCE: 63
tttctcgagc cagatgagct gtatttatta ctggaacg        38

<210> SEQ ID NO 64
<211> LENGTH: 30
<212> TYPE: DNA
<213> ORGANISM: Artificial Sequence
<220> FEATURE:
<223> OTHER INFORMATION: PCR primer

<400> SEQUENCE: 64
ttggatccat ggggcaaccc gggaacggca        30

<210> SEQ ID NO 65

```
<211> LENGTH: 34
<212> TYPE: DNA
<213> ORGANISM: Artificial Sequence
<220> FEATURE:
<223> OTHER INFORMATION: PCR primer

<400> SEQUENCE: 65
tttctcgagc ccagcagtga gtcatttgta ctac                          34

<210> SEQ ID NO 66
<211> LENGTH: 32
<212> TYPE: DNA
<213> ORGANISM: Artificial Sequence
<220> FEATURE:
<223> OTHER INFORMATION: PCR primer

<400> SEQUENCE: 66
ttggatccat ggaggaaggt ggtgattttg ac                            32

<210> SEQ ID NO 67
<211> LENGTH: 32
<212> TYPE: DNA
<213> ORGANISM: Artificial Sequence
<220> FEATURE:
<223> OTHER INFORMATION: PCR primer

<400> SEQUENCE: 67
tttctcgagc cgtcaaccac aagggtctcc tg                            32

<210> SEQ ID NO 68
<211> LENGTH: 31
<212> TYPE: DNA
<213> ORGANISM: Artificial Sequence
<220> FEATURE:
<223> OTHER INFORMATION: PCR primer

<400> SEQUENCE: 68
tttaagctta tggagctgct aaagctgaac c                             31

<210> SEQ ID NO 69
<211> LENGTH: 32
<212> TYPE: DNA
<213> ORGANISM: Artificial Sequence
<220> FEATURE:
<223> OTHER INFORMATION: PCR primer

<400> SEQUENCE: 69
tttctcgagc cgccagggcc cagtgtgctg at                            32

<210> SEQ ID NO 70
<211> LENGTH: 1629
<212> TYPE: DNA
<213> ORGANISM: Pyrearinus termitilluminans

<400> SEQUENCE: 70
atggagagag agaagaacgt ggtgtacggc cccgagccca agcaccctct gggcaacttc      60
accgccggcg agatgctgta caacgctctg cacaagcact cccacatccc ccaggccatc     120
ctggacgtga tgggcaacga gtcccttttc taccaggagt tcttcgacac tactgtgaag     180
ctgggccaga gcctccagaa ctgtggctac aagatgaacg atgtcgtgtc gatctgtgca     240
gagaacaaca agagattctt catccccatc atctccgcct ggtacatcgg catggtggtg     300
gcccctgtga acgaggacta tatcccagac gagctgtgta agtgaccgg  catctccaag     360 ccgatcctgg tcttcaccac taggaagatc ctgcctaagg ttttggaggt taaagacaga     420
```

```
accaactaca taaagaggat catcatactg gactctgaag agaacctgct gggctgcgag      480
agcctgcaca acttcatgtc caggtactcc gacaacaacc tccaaacatt caagcctctg      540
cactacgacc ctgtggacca ggtagccgcc atcctgtgct cctccggcac aaccggcctg      600
cctaaaggcg tgatgcagac ccacaggaac atctgtgtga gactcacaca cgcatctgac      660
cccagagtgg gtacacaact catccccggc gtatccgtgc tggcctacct gccattcttc      720
cacgccttcg gcttcagtat caacctgggc tatttcatgg tgggcctgag agtggtgatg      780
ctccgaaggt ttaaccagga ggtgttcctg aaggccatcc aggactacga ggtgaggagc      840
gtgatcaacg ttccctccac aatcctgttc ctgtccaaga gccctctggt ggacaagtac      900
gacctatcca ccctggcgga gctgtgctgt ggagccgctc ctctggcgaa ggaggtggcc      960
gagatcgccg tgaagaggct gaacctgcca gggatacggt gtggctacgg tctaacagag     1020
tctacctccg ccaacatcca tactctgcac aacgagttca agtccggctc cctgggcaag     1080
gtgacacctt acatggccgc caagatcatc gacaggaaca ccggcgaggc cctgggtcca     1140
aaccaggtgg gcgagctgtg catctgggga cctatggtaa caaaaggcta tgtgaacaac     1200
ccacaggcta ctaaggaggc catcgacgac gacggctggc tgcactctgg cgacttcggc     1260
tactacgacg aggacgagta tttctacatc gtggaccggt acaaggagct gatcaaatac     1320
aagggctatc aggtcgcccc tgtggagctg gaggagatcc tccttcagca cccaggcatc     1380
agggacgtgg ccgtcgtggg tatccctgac atcgaggccg cgagctgcc agccggcttc     1440 gtggtgaagc agcccggcgc ccaactcacc gctaaggagg tgtacgactt cctggcccag     1500
agggtgtctc actccaagta cctgagggc ggcgtaaggt tcgtggactc tatccccagg     1560
aacgtgacag gcaagattag tcgaaaagag ctgagggagg ccctgatgga gaaggcttct     1620
aagctgtaa                                                             1629
```

<210> SEQ ID NO 71
<211> LENGTH: 542
<212> TYPE: PRT
<213> ORGANISM: Pyrearinus termitilluminans

<400> SEQUENCE: 71

```
Met Glu Arg Glu Lys Asn Val Val Tyr Gly Pro Glu Pro Lys His Pro
1               5                   10                  15

Leu Gly Asn Phe Thr Ala Gly Glu Met Leu Tyr Asn Ala Leu His Lys
            20                  25                  30

His Ser His Ile Pro Gln Ala Ile Leu Asp Val Met Gly Asn Glu Ser
        35                  40                  45

Leu Ser Tyr Gln Glu Phe Phe Asp Thr Thr Val Lys Leu Gly Gln Ser
    50                  55                  60

Leu Gln Asn Cys Gly Tyr Lys Met Asn Asp Val Val Ser Ile Cys Ala
65                  70                  75                  80

Glu Asn Asn Lys Arg Phe Phe Ile Pro Ile Ser Ala Trp Tyr Ile
                85                  90                  95

Gly Met Val Val Ala Pro Val Asn Glu Asp Tyr Ile Pro Asp Glu Leu
            100                 105                 110

Cys Lys Val Thr Gly Ile Ser Lys Pro Ile Leu Val Phe Thr Thr Arg
        115                 120                 125

Lys Ile Leu Pro Lys Val Leu Glu Val Lys Asp Arg Thr Asn Tyr Ile
    130                 135                 140
```

-continued

```
Lys Arg Ile Ile Ile Leu Asp Ser Glu Glu Asn Leu Leu Gly Cys Glu
145                 150                 155                 160

Ser Leu His Asn Phe Met Ser Arg Tyr Ser Asp Asn Asn Leu Gln Thr
            165                 170                 175

Phe Lys Pro Leu His Tyr Asp Pro Val Asp Gln Val Ala Ala Ile Leu
        180                 185                 190

Cys Ser Ser Gly Thr Thr Gly Leu Pro Lys Gly Val Met Gln Thr His
    195                 200                 205

Arg Asn Ile Cys Val Arg Leu Thr His Ala Ser Asp Pro Arg Val Gly
210                 215                 220

Thr Gln Leu Ile Pro Gly Val Ser Val Leu Ala Tyr Leu Pro Phe Phe
225                 230                 235                 240

His Ala Phe Gly Phe Ser Ile Asn Leu Gly Tyr Phe Met Val Gly Leu
            245                 250                 255

Arg Val Val Met Leu Arg Arg Phe Asn Gln Glu Val Phe Leu Lys Ala
            260                 265                 270

Ile Gln Asp Tyr Glu Val Arg Ser Val Ile Asn Val Pro Ser Thr Ile
        275                 280                 285

Leu Phe Leu Ser Lys Ser Pro Leu Val Asp Lys Tyr Asp Leu Ser Thr
    290                 295                 300

Leu Ala Glu Leu Cys Cys Gly Ala Ala Pro Leu Ala Lys Glu Val Ala
305                 310                 315                 320

Glu Ile Ala Val Lys Arg Leu Asn Leu Pro Gly Ile Arg Cys Gly Tyr
            325                 330                 335

Gly Leu Thr Glu Ser Thr Ser Ala Asn Ile His Thr Leu His Asn Glu
            340                 345                 350

Phe Lys Ser Gly Ser Leu Gly Lys Val Thr Pro Tyr Met Ala Ala Lys
        355                 360                 365

Ile Ile Asp Arg Asn Thr Gly Glu Ala Leu Gly Pro Asn Gln Val Gly
    370                 375                 380

Glu Leu Cys Ile Trp Gly Pro Met Val Thr Lys Gly Tyr Val Asn Asn
385                 390                 395                 400

Pro Gln Ala Thr Lys Glu Ala Ile Asp Asp Asp Gly Trp Leu His Ser
            405                 410                 415

Gly Asp Phe Gly Tyr Tyr Asp Glu Asp Glu Tyr Phe Tyr Ile Val Asp
            420                 425                 430

Arg Tyr Lys Glu Leu Ile Lys Tyr Lys Gly Tyr Gln Val Ala Pro Val
        435                 440                 445

Glu Leu Glu Glu Ile Leu Leu Gln His Pro Gly Ile Arg Asp Val Ala
    450                 455                 460

Val Val Gly Ile Pro Asp Ile Glu Ala Gly Glu Leu Pro Ala Gly Phe
465                 470                 475                 480

Val Val Lys Gln Pro Gly Ala Gln Leu Thr Ala Lys Glu Val Tyr Asp
            485                 490                 495

Phe Leu Ala Gln Arg Val Ser His Ser Lys Tyr Leu Arg Gly Gly Val
            500                 505                 510

Arg Phe Val Asp Ser Ile Pro Arg Asn Val Thr Gly Lys Ile Ser Arg
        515                 520                 525

Lys Glu Leu Arg Glu Ala Leu Met Glu Lys Ala Ser Lys Leu
    530                 535                 540
```